(12) United States Patent
Coe et al.

(10) Patent No.: US 9,242,406 B2
(45) Date of Patent: Jan. 26, 2016

(54) APPARATUS AND PROCESS FOR APERTURING AND STRETCHING A WEB

(75) Inventors: Richard George Coe, Cincinnati, OH (US); Jill Marlene Orr, Liberty Township, OH (US); Sarah Beth Gross, Harrison, OH (US); Robert Karl Isburgh, Symmes, OH (US); Leroy Joseph Kocher, Sunman, IN (US); Kevin Gerard Muhs, Cincinnati, OH (US); Timothy Ian Mullane, Union, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 899 days.

(21) Appl. No.: 13/455,857

(22) Filed: Apr. 25, 2012

(65) Prior Publication Data

US 2012/0282436 A1 Nov. 8, 2012

Related U.S. Application Data

(63) Continuation-in-part of application No. 13/094,195, filed on Apr. 26, 2011, now Pat. No. 8,657,596.

(51) Int. Cl.
*B29C 55/18* (2006.01)
*B29C 55/08* (2006.01)
*B29C 59/04* (2006.01)
(Continued)

(52) U.S. Cl.
CPC ............ *B29C 55/18* (2013.01); *A61F 13/15577* (2013.01); *B29C 55/08* (2013.01); *B29C 59/04* (2013.01); *B31F 1/07* (2013.01); *B29C 43/226* (2013.01); *B29C 53/22* (2013.01); *B29C 53/265* (2013.01); *B29C 53/285* (2013.01); *B31F 2201/0733* (2013.01); *B31F 2201/0738* (2013.01); *B31F 2201/0743* (2013.01);
(Continued)

(58) Field of Classification Search
None
See application file for complete search history.

(56) References Cited

U.S. PATENT DOCUMENTS 2,068,456 A 1/1937 Hooper
2,275,425 A 3/1942 Grabec
(Continued)

FOREIGN PATENT DOCUMENTS

EP 509012 10/1992
EP 598970 A1 6/1994
(Continued)

OTHER PUBLICATIONS

U.S. Appl. No. 12/188,527, filed Aug. 8, 2008, Hammons.
(Continued)

*Primary Examiner* — Jeffrey Wollschlager
(74) *Attorney, Agent, or Firm* — Megan C. Hymore; George H. Leal

(57) ABSTRACT

Apparatuses and processes for aperturing and stretching a web are disclosed. In one embodiment, the method involves feeding a web into a nip that is formed between at least one pair of intermeshing rolls. The first roll is a raised ridge rotary knife aperturing roll and the second roll is a ring roll; both rolls comprise ridges and grooves. The first roll comprises a plurality of spaced-apart teeth extending outwardly from the top surface of the ridges, said teeth having tips, wherein the top surface of said ridges are disposed between the tips of said teeth and the bottom surface of said grooves. These apparatuses and processes enable a web to be formed which comprises apertures having greater open area than previously achievable with traditional processes and apparatuses.

5 Claims, 15 Drawing Sheets

(51) Int. Cl.
*A61F 13/15* (2006.01)
*B31F 1/07* (2006.01)
*B29C 53/26* (2006.01)
*B29C 43/22* (2006.01)
*B29C 53/28* (2006.01)
*B29C 53/22* (2006.01)

(52) U.S. Cl.
CPC .. *B31F2201/0797* (2013.01); *Y10T 428/24273* (2015.01)

(56) References Cited

U.S. PATENT DOCUMENTS

| | | |
|---|---|---|
| 2,404,758 A | 7/1946 | Teague et al. |
| 2,633,441 A | 3/1953 | Buttress |
| 2,748,863 A | 6/1956 | Benton |
| 2,924,863 A | 2/1960 | Chavannes |
| 3,034,180 A | 5/1962 | Greiner et al. |
| 3,073,304 A | 1/1963 | Schaar |
| 3,081,500 A | 3/1963 | Griswold et al. |
| 3,081,512 A | 3/1963 | Griswold |
| 3,137,893 A | 6/1964 | Gelpke |
| 3,355,974 A | 12/1967 | Carmichael |
| 3,511,740 A | 5/1970 | Sanders |
| 3,539,423 A | 11/1970 | Simison et al. |
| 3,542,634 A | 11/1970 | Such et al. |
| 3,549,742 A | 12/1970 | Benz |
| 3,566,726 A | 3/1971 | Politis |
| 3,579,763 A | 5/1971 | Sommer |
| 3,681,182 A | 8/1972 | Kalwaites |
| 3,681,183 A | 8/1972 | Kalwaites |
| 3,684,284 A | 8/1972 | Tranfield |
| 3,695,270 A | 10/1972 | Dostal |
| 3,718,059 A | 2/1973 | Clayton |
| 3,760,671 A | 9/1973 | Jenkins |
| 3,881,987 A | 5/1975 | Benz |
| 3,949,127 A | 4/1976 | Ostermeier et al. |
| 3,965,906 A | 6/1976 | Karami |
| 4,035,881 A | 7/1977 | Zocher |
| 4,042,453 A | 8/1977 | Conway et al. |
| 4,135,021 A | 1/1979 | Patchell et al. |
| 4,276,336 A | 6/1981 | Sabee |
| 4,379,799 A | 4/1983 | Holmes et al. |
| 4,397,644 A | 8/1983 | Matthews et al. |
| 4,465,726 A | 8/1984 | Holmes et al. |
| 4,469,734 A | 9/1984 | Minto et al. |
| 4,514,345 A | 4/1985 | Johnson et al. |
| 4,528,239 A | 7/1985 | Trokhan |
| 4,529,480 A | 7/1985 | Trokhan |
| 4,588,630 A | 5/1986 | Shimalla |
| 4,741,941 A | 5/1988 | Englebert et al. |
| 4,758,297 A | 7/1988 | Calligarich |
| 4,781,962 A | 11/1988 | Zamarripa et al. |
| 4,798,604 A | 1/1989 | Carter |
| 4,820,294 A | 4/1989 | Morris |
| 4,840,829 A | 6/1989 | Suzuki et al. |
| 4,859,519 A | 8/1989 | Cabe, Jr. et al. |
| 4,886,632 A | 12/1989 | Van Iten et al. |
| 4,935,087 A | 6/1990 | Gilman |
| 4,953,270 A | 9/1990 | Gilpatrick |
| 5,019,062 A | 5/1991 | Ryan et al. |
| 5,062,418 A | 11/1991 | Dyer et al. |
| 5,144,730 A | 9/1992 | Dilo |
| 5,165,979 A | 11/1992 | Watkins et al. |
| 5,171,238 A | 12/1992 | Kajander |
| 5,180,620 A | 1/1993 | Mende |
| 5,188,625 A | 2/1993 | Van Iten et al. |
| 5,223,319 A | 6/1993 | Cotton et al. |
| 5,242,632 A | 9/1993 | Mende |
| 5,328,565 A | 7/1994 | Rasch et al. |
| 5,382,245 A | 1/1995 | Thompson et al. |
| 5,383,870 A | 1/1995 | Takai et al. |
| 5,387,209 A | 2/1995 | Yamamoto et al. |
| 5,414,914 A | 5/1995 | Suzuki et al. |
| 5,415,640 A | 5/1995 | Kirby et al. |
| 5,429,854 A | 7/1995 | Currie et al. |
| 5,437,653 A | 8/1995 | Gilman et al. |
| 5,470,326 A | 11/1995 | Dabi et al. |
| 5,503,715 A | 4/1996 | Trokhan et al. |
| 5,508,080 A | 4/1996 | Sorimachi et al. |
| 5,518,801 A | 5/1996 | Chappell et al. |
| 5,533,991 A | 7/1996 | Kirby et al. |
| 5,534,326 A | 7/1996 | Trokhan et al. |
| 5,554,145 A | 9/1996 | Roe et al. |
| 5,560,794 A | 10/1996 | Currie et al. |
| 5,567,501 A | 10/1996 | Srinivasan et al. |
| D375,844 S | 11/1996 | Edwards et al. |
| 5,573,719 A | 11/1996 | Fitting |
| 5,575,874 A | 11/1996 | Griesbach, III et al. |
| 5,580,418 A | 12/1996 | Alikhan |
| 5,599,420 A | 2/1997 | Yeo et al. |
| 5,624,427 A | 4/1997 | Bergman et al. |
| 5,626,571 A | 5/1997 | Young et al. |
| 5,628,097 A | 5/1997 | Benson et al. |
| 5,637,194 A | 6/1997 | Ampulski et al. |
| 5,648,142 A | 7/1997 | Phillips |
| 5,656,119 A | 8/1997 | Srinivasan et al. |
| 5,658,639 A | 8/1997 | Curro et al. |
| 5,667,619 A | 9/1997 | Alikhan |
| 5,667,625 A | 9/1997 | Alikhan |
| 5,691,035 A | 11/1997 | Chappell et al. |
| 5,700,255 A | 12/1997 | Curro et al. |
| 5,704,101 A | 1/1998 | Majors et al. |
| 5,709,829 A | 1/1998 | Giacometti |
| 5,714,041 A | 2/1998 | Huston |
| 5,714,107 A | 2/1998 | Levy et al. |
| 5,723,087 A | 3/1998 | Chappell et al. |
| 5,743,776 A | 4/1998 | Igaue et al. |
| 5,804,021 A | 9/1998 | Abuto et al. |
| 5,814,389 A | 9/1998 | Giacometti |
| 5,817,394 A | 10/1998 | Alikhan et al. |
| 5,841,107 A | 11/1998 | Riva |
| 5,858,504 A | 1/1999 | Fitting |
| 5,879,494 A | 3/1999 | Hoff et al. |
| 5,891,544 A | 4/1999 | Chappell et al. |
| 5,895,623 A | 4/1999 | Trokhan et al. |
| 5,900,122 A | 5/1999 | Huston |
| 5,906,710 A | 5/1999 | Trokhan |
| 5,914,084 A | 6/1999 | Benson et al. |
| 5,916,661 A | 6/1999 | Benson et al. |
| 5,919,177 A | 7/1999 | Georger et al. |
| 5,925,026 A | 7/1999 | Arteman et al. |
| 5,935,381 A | 8/1999 | Trokhan et al. |
| 5,964,742 A | 10/1999 | McCormack et al. |
| 5,968,029 A | 10/1999 | Chappell et al. |
| 5,986,167 A | 11/1999 | Arteman et al. |
| 5,993,432 A | 11/1999 | Lodge et al. |
| 6,007,468 A | 12/1999 | Giacometti |
| 6,025,050 A | 2/2000 | Srinivasan et al. |
| 6,027,483 A | 2/2000 | Chappell et al. |
| 6,039,555 A | 3/2000 | Tsuji et al. |
| 6,080,276 A | 6/2000 | Burgess |
| 6,096,016 A | 8/2000 | Tsuji et al. |
| 6,114,263 A | 9/2000 | Benson et al. |
| 6,117,524 A | 9/2000 | Hisanaka et al. |
| 6,120,718 A | 9/2000 | Kotek et al. |
| 6,129,801 A | 10/2000 | Benson et al. |
| 6,136,146 A | 10/2000 | Phan et al. |
| 6,155,083 A | 12/2000 | Goeser et al. |
| 6,168,849 B1 | 1/2001 | Braverman et al. |
| 6,176,954 B1 | 1/2001 | Tsuji et al. |
| 6,247,914 B1 | 6/2001 | Lindquist et al. |
| D444,631 S | 7/2001 | Woodbridge et al. |
| 6,264,872 B1 | 7/2001 | Majors et al. |
| 6,287,407 B1 | 9/2001 | Stein et al. |
| 6,383,431 B1 | 5/2002 | Dobrin et al. |
| 6,395,122 B1 | 5/2002 | Hisanaka et al. |
| 6,395,211 B1 | 5/2002 | Dettmer et al. |
| 6,398,895 B1 | 6/2002 | Stein et al. |
| 6,410,823 B1 | 6/2002 | Daley et al. |
| 6,420,625 B1 | 7/2002 | Jones et al. |
| 6,423,884 B1 | 7/2002 | Oehmen |
| 6,444,089 B1 | 9/2002 | Hollmark et al. |
| 6,451,718 B1 | 9/2002 | Yamada et al. |

(56) References Cited

U.S. PATENT DOCUMENTS

| | | |
|---|---|---|
| 6,452,064 B1 | 9/2002 | Thoren et al. |
| 6,454,905 B1 | 9/2002 | Hollmark et al. |
| 6,458,447 B1 | 10/2002 | Cabell et al. |
| 6,464,831 B1 | 10/2002 | Trokhan et al. |
| D466,702 S | 12/2002 | Carlson et al. |
| 6,503,370 B2 | 1/2003 | Hollmark et al. |
| 6,506,329 B1 | 1/2003 | Curro et al. |
| 6,537,936 B1 | 3/2003 | Busam et al. |
| 6,596,127 B2 | 7/2003 | Hollmark et al. |
| 6,620,485 B1 | 9/2003 | Benson et al. |
| 6,632,504 B1 | 10/2003 | Gillespie et al. |
| D481,872 S | 11/2003 | Hennel et al. |
| 6,647,549 B2 | 11/2003 | McDevitt et al. |
| 6,669,878 B2 | 12/2003 | Konishi et al. |
| 6,716,498 B2 | 4/2004 | Curro et al. |
| 6,726,870 B1 | 4/2004 | Benson et al. |
| 6,736,916 B2 | 5/2004 | Steinke et al. |
| 6,787,000 B2 | 9/2004 | Burazin et al. |
| 6,794,626 B2 | 9/2004 | Kiermeier et al. |
| 6,808,791 B2 | 10/2004 | Curro et al. |
| 6,811,652 B2 | 11/2004 | Hollmark |
| 6,818,101 B2 | 11/2004 | Vinson et al. |
| 6,818,802 B2 | 11/2004 | Takai et al. |
| 6,830,800 B2 | 12/2004 | Curro et al. |
| 6,837,956 B2 | 1/2005 | Cowell et al. |
| 6,855,220 B2 | 2/2005 | Wildeman |
| 6,863,960 B2 | 3/2005 | Curro et al. |
| 6,872,274 B2 | 3/2005 | Kauschke et al. |
| 6,884,494 B1 | 4/2005 | Curro et al. |
| 6,989,075 B1 | 1/2006 | Kao et al. |
| 6,991,706 B2 | 1/2006 | Lindsay et al. |
| 7,005,558 B1 | 2/2006 | Johansson et al. |
| 7,037,569 B2 | 5/2006 | Curro et al. |
| 7,399,378 B2 | 7/2008 | Edwards et al. |
| 7,811,665 B2 | 10/2010 | Manifold |
| 7,820,874 B2 | 10/2010 | Manifold |
| 7,824,594 B2 * | 11/2010 | Qureshi et al. ............ 264/288.4 |
| 7,939,168 B2 | 5/2011 | Manifold |
| 7,960,020 B2 | 6/2011 | Manifold |
| 7,967,801 B2 | 6/2011 | Hammons |
| 7,989,058 B2 | 8/2011 | Manifold |
| 7,993,317 B2 | 8/2011 | Hammons |
| 8,012,309 B2 | 9/2011 | Pare et al. |
| 8,025,966 B2 | 9/2011 | Manifold |
| 8,058,501 B2 | 11/2011 | Hammons |
| 8,152,957 B2 | 4/2012 | Edwards et al. |
| 8,158,043 B2 | 4/2012 | Gibson |
| 2002/0039867 A1 | 4/2002 | Curro et al. |
| 2002/0055310 A1 | 5/2002 | Falk et al. |
| 2002/0103469 A1 | 8/2002 | Chen et al. |
| 2002/0105110 A1 | 8/2002 | Dobrin et al. |
| 2002/0107495 A1 | 8/2002 | Chen et al. |
| 2002/0119720 A1 | 8/2002 | Arora et al. |
| 2002/0132544 A1 | 9/2002 | Takagaki |
| 2003/0021951 A1 | 1/2003 | Desai et al. |
| 2003/0028165 A1 | 2/2003 | Curro et al. |
| 2003/0085213 A1 | 5/2003 | Burckhardt et al. |
| 2003/0191442 A1 | 10/2003 | Bewick-Sonntag et al. |
| 2003/0191443 A1 | 10/2003 | Taylor et al. |
| 2004/0091563 A1* | 5/2004 | Saito et al. ................. 425/363 |
| 2004/0121686 A1 | 6/2004 | Wong et al. |
| 2004/0122396 A1 | 6/2004 | Maldonado et al. |
| 2004/0126531 A1 | 7/2004 | Harvey et al. |
| 2004/0131820 A1 | 7/2004 | Turner et al. |
| 2004/0137200 A1 | 7/2004 | Chhabra et al. |
| 2004/0157036 A1 | 8/2004 | Provost et al. |
| 2004/0229008 A1 | 11/2004 | Hoying et al. |
| 2004/0242097 A1 | 12/2004 | Hasenoehrl et al. |
| 2004/0265533 A1 | 12/2004 | Hoying et al. |
| 2004/0265534 A1* | 12/2004 | Curro et al. .................. 428/92 |
| 2005/0051290 A1 | 3/2005 | Beasley, Jr. et al. |
| 2005/0064136 A1 | 3/2005 | Turner |
| 2005/0096614 A1 | 5/2005 | Perez et al. |
| 2005/0123726 A1 | 6/2005 | Broering et al. |
| 2005/0140057 A1* | 6/2005 | Gerndt .......................... 264/284 |
| 2006/0019056 A1 | 1/2006 | Turner et al. |
| 2006/0087053 A1* | 4/2006 | O'Donnell et al. ........... 264/156 |
| 2007/0131368 A1 | 6/2007 | Xia |
| 2008/0217809 A1* | 9/2008 | Zhao et al. .................... 264/229 |
| 2010/0036346 A1* | 2/2010 | Hammons et al. ............ 604/378 |
| 2010/0201024 A1* | 8/2010 | Gibson et al. ................. 264/156 |
| 2011/0088859 A1 | 4/2011 | Hultcrantz et al. |
| 2012/0049404 A1 | 3/2012 | Gibson |
| 2012/0064280 A1 | 3/2012 | Hammons et al. |
| 2012/0064298 A1 | 3/2012 | Orr et al. |
| 2012/0273146 A1 | 11/2012 | Curro et al. |
| 2012/0273148 A1 | 11/2012 | Orr et al. |
| 2012/0273990 A1 | 11/2012 | O'Donnell et al. |
| 2012/0276238 A1 | 11/2012 | Strube et al. |
| 2012/0276341 A1 | 11/2012 | Lake et al. |
| 2012/0276637 A1 | 11/2012 | Zhou et al. |
| 2012/0277393 A1 | 11/2012 | Curro et al. |
| 2012/0277704 A1 | 11/2012 | Marinelli et al. |
| 2012/0277705 A1 | 11/2012 | Marinelli et al. |
| 2012/0277706 A1 | 11/2012 | Marinelli et al. |
| 2012/0277707 A1 | 11/2012 | Orr et al. |
| 2012/0277708 A1 | 11/2012 | Marinelli et al. |
| 2012/0277709 A1 | 11/2012 | Marinelli et al. |
| 2012/0277710 A1 | 11/2012 | Marinelli et al. |
| 2012/0295060 A1 | 11/2012 | Mullane |

FOREIGN PATENT DOCUMENTS

| | | |
|---|---|---|
| EP | 955159 A1 | 11/1999 |
| EP | 963747 A1 | 12/1999 |
| EP | 1004412 A1 | 5/2000 |
| GB | 900083 A | 7/1962 |
| WO | 9515138 A1 | 6/1995 |
| WO | 02100632 A1 | 12/2002 |
| WO | 2005011936 A1 | 2/2005 |

OTHER PUBLICATIONS

U.S. Appl. No. 13/094,195, filed Apr. 26, 2011, Lake.
U.S. Appl. No. 13/094,295, filed Apr. 26, 2011, Marinelli.
U.S. Appl. No. 13/094,310, filed Apr. 26, 2011, Orr.
U.S. Appl. No. 13/094,477, filed Apr. 26, 2011, Stone.
U.S. Appl. No. 13/094,559, filed Apr. 26, 2011, Coe.
U.S. Appl. No. 13/094,593, filed Apr. 26, 2011, Stone.
PCT International Search Report, mailed Dec. 17, 2013, 11 pages.

* cited by examiner

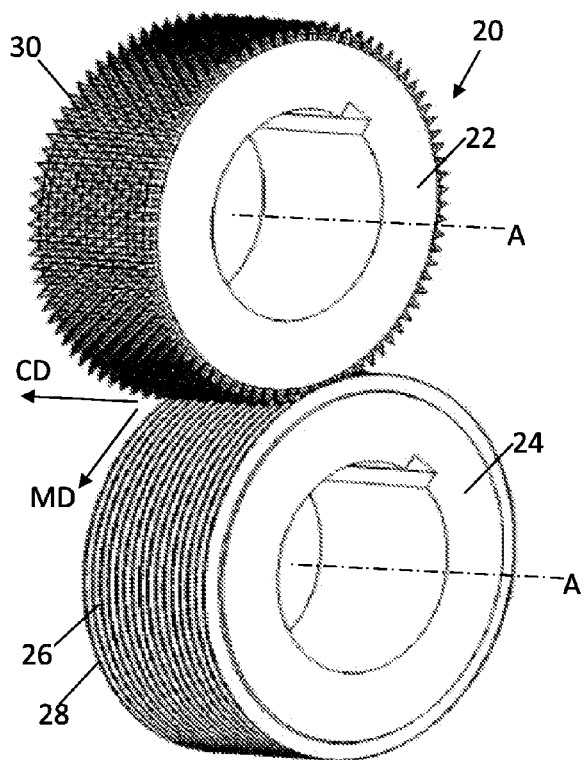
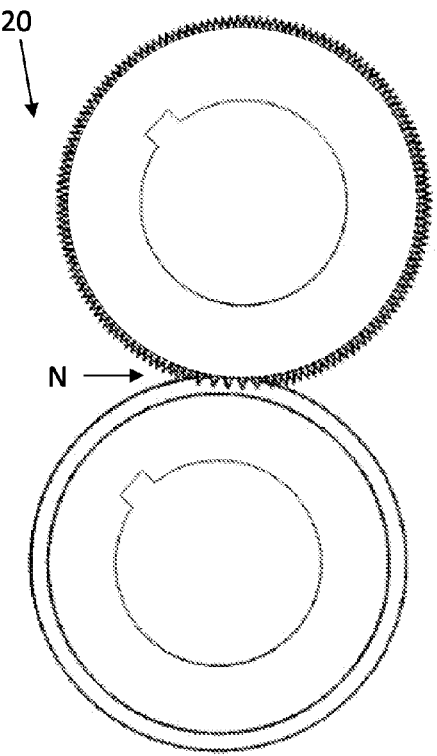
Fig. 2A
PRIOR ART
Fig. 2B
PRIOR ART
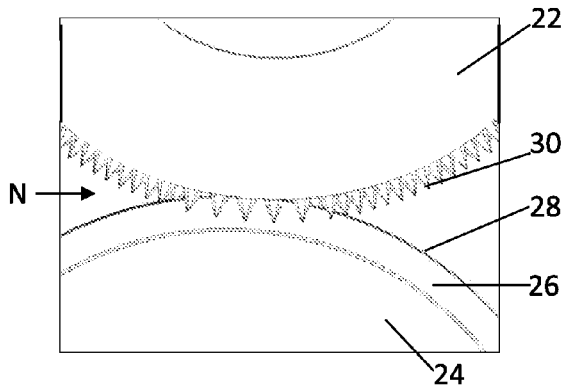
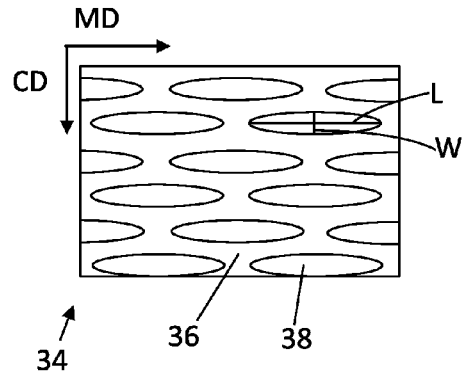
Fig. 2C
PRIOR ART
Fig. 2D
PRIOR ART

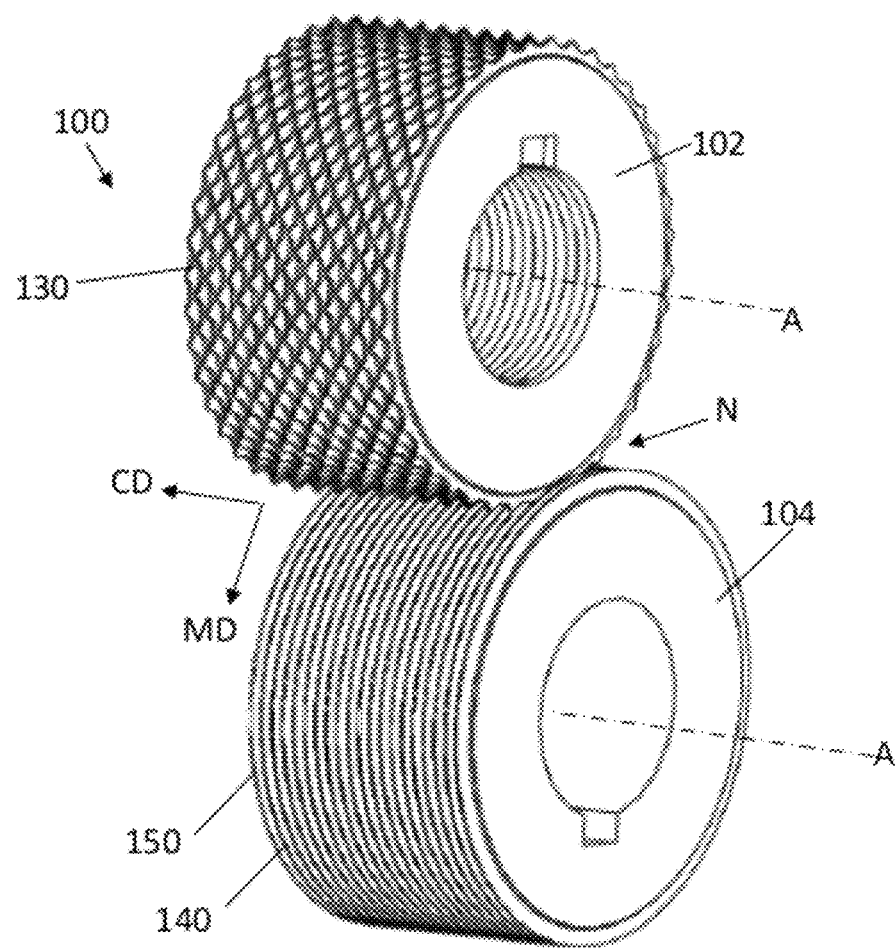
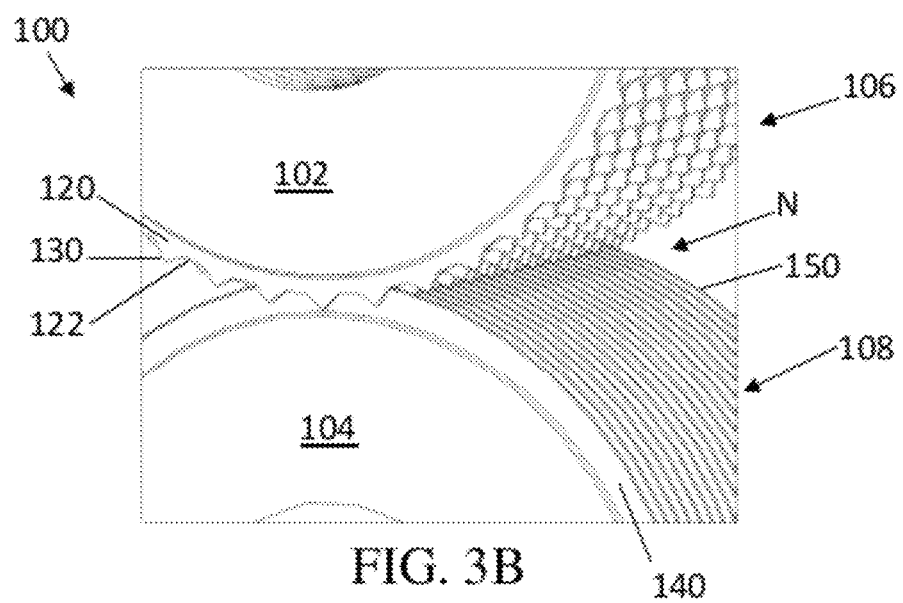
FIG. 3A
FIG. 3B

APPARATUS AND PROCESS FOR APERTURING AND STRETCHING A WEB

CROSS REFERENCE TO RELATED APPLICATION

This application is a continuation-in-part of application Ser. No. 13/094,195 U.S. Pat. No. 8,657,596 which was filed on Apr. 26, 2011.

FIELD OF THE INVENTION

The present invention is directed to apertured web materials and apparatuses and methods for aperturing and stretching a web to create such materials.

BACKGROUND OF THE INVENTION

Various methods and apparatuses for aperturing, deforming, and/or stretching webs are disclosed in the patent literature. With an aperturing method such as rotary knife aperturing, it is difficult to produce a web having closely-spaced apertures wherein the apertures have desirable widths in the cross-machine direction ("CD"). In order to space aperture rows close together, activation teeth may be provided which have a very small included angle. However, this approach poses a problem because apertures are produced which do not have sufficient aperture width in the CD, even at high engagement depths (the interference of an activation tooth roll with a mating ring roll). The resultant apertures are often elongated in the machine direction—leading to a slit-like appearance, low open area, and potential stress concentrations which cause in-use tearing. Creating slit-like, low-open-area apertures is particularly problematic as tougher and more tear-resistant webs are utilized. Rounded or tapered hot-pin aperturing is common, but has the drawback of requiring greater registration precision for the mating rolls, and it typically results in greater aperture spacing. Rounded or tapered hot-pin aperturing is typically run at lower linear speeds.

Post ring-rolling an apertured web to stretch it is possible, but can result in alternating rows of aperture sizes since apertures cannot be lined up with the subsequent ring roll stretching process. It is difficult to align features in the cross direction with later processes due to variable spreading of the substrate. Post ring-rolling can also significantly weaken the web, making it more prone to tearing.

It is desirable to produce a web having discrete, closely-spaced apertures wherein the apertures have larger CD widths than previously possible. A need exists for an apertured web which is stronger in the cross-machine direction so it doesn't easily tear in the cross-machine direction. A need exists for a method of producing an apertured web having larger, wider, more open apertures. A need also exists for apparatuses that will allow a web to be apertured with the apertures having desired, larger-widths in the cross-machine direction.

There are many known processes for creating a web with ridges and grooves, for example ring rolling. There are also many know processes for creating a web with apertures, for example, hot pin aperturing. However, it is difficult to produce a corrugated web having alternating ridges and grooves which are registered to a specific aperture pattern. Processes exist for micro-aperturing followed by ring-rolling; however, this results in flattened webs with no corrugation. A web with ridges and grooves (flat strips) may be formed via air-jetting or water jetting on a patterned belt. However, air-jetting or water jetting are much slower processes and requires more energy than the invention described herein. In addition, the ridges are not hollow and can retain more fluid.

It is desirable to produce a web having alternating ridges and grooves wherein apertures are located in specific positions in the web, for instance, in the grooves or in the ridges. A need exists for an apertured web which comprises a registered corrugation pattern.

These are all goals of the present invention; embodiments described herein may achieve various combinations of these goals. A particular embodiment may, but need not, embody every goal.

SUMMARY OF THE INVENTION

The present inventions are directed to apertured—and often corrugated—web materials and apparatuses and methods for aperturing a web to create such materials. Such materials can be provided as members of products such as absorbent articles (such as topsheets, backsheets, acquisition layers, liquid handling layers, and absorbent cores), packaging (such as flow wrap, shrink wrap, and polybags), wipes, facial tissue, toilet tissue, paper towels, and the like. There are numerous non-limiting embodiments of the present invention.

The present inventions relate to an apparatus comprising two intermeshing forming structures that form a nip therebetween, said apparatus comprising: a first forming structure comprising: a plurality of first ridges and first grooves on the surface of the forming structure, wherein said first ridges have a top surface and said first grooves have a bottom surface; and a plurality of spaced-apart teeth extending outwardly from the top surface of said first ridges, each tooth being capable of forming an aperture, wherein the top surface of said first ridge is located between the tips of said teeth and the bottom surface of said first grooves; and a second forming structure comprising a plurality of continuous second ridges and second grooves.

The present inventions further relate to an apparatus comprising two intermeshing counter-rotating rolls that form a nip therebetween, said apparatus comprising a generally cylindrical first roll, said first roll having a surface, a circumference, and an axis, said first roll comprising: a plurality of circumferential first ridges and circumferential first grooves on the surface of the roll, wherein said first ridges have a top surface and said first grooves have a bottom surface; and a plurality of spaced-apart teeth extending outwardly from the top surface of said first ridges, each tooth tapering from the top surface to a tip, wherein the top surface of said first ridge is located between the tips of said teeth and the bottom surface of said first grooves; and a generally cylindrical second roll, said second roll comprising a plurality of continuous, circumferential second ridges and second grooves.

The present inventions further relate to a process for deforming a web using an apparatus, the process comprising feeding a precursor web into a nip that is formed between two intermeshing rolls comprising: a) a generally cylindrical first roll, said first roll having a surface, a circumference, and an axis, said first roll comprising: a plurality of first ridges and first grooves extending around the circumference of the roll on the surface of the roll, wherein said first ridges have a top surface and said first grooves have a bottom surface; and a plurality of spaced-apart teeth extending outwardly from the top surface of said first ridges, said teeth having tips, wherein the top surface of said first ridges are disposed between the tips of said teeth and the bottom surface of said first grooves; and b) a generally cylindrical second roll, said second roll comprising a plurality of continuous, circumferential ridges and grooves, wherein said second ridges have a top surface and said second grooves have a bottom surface; wherein when said web is fed into said nip, the top of at least some of the ridges on the first roll extend inward toward the axis of said second roll to a depth beyond the top of at least some of the second ridges on said second roll, and said web is: (i) apertured by said teeth in a plurality of spaced-apart first locations to form a plurality of spaced-apart apertures; and (ii) stretched in the cross-machine direction by said intermeshing rolls.

BRIEF DESCRIPTION OF THE DRAWINGS

The accompanying drawings are included to provide a further understanding of the present inventions. The drawings illustrate the present inventions described herein, and together with the description, serve to explain the claimed subject matter.

FIG. 2A is a perspective view of a prior art pair of rolls—a rotary knife aperturing (or "RKA") roll and a ring roll—for aperturing a web.

FIG. 2B is a side view of the pair of prior art rolls shown in FIG. 2A.

FIG. 2C is an enlarged side view of the nip between the rolls shown in FIG. 2A.

FIG. 2D is a top view of an exemplary prior art web that can be formed by using the rolls shown in FIG. 2A.

FIG. 3A is a perspective view of a pair of rolls for use in the apparatuses and processes described herein, in which one roll is a staggered "raised ridge" RKA roll and the other roll is a ring roll.

FIG. 3B is an enlarged side view of the nip between the rolls shown in FIG. 3A.

DETAILED DESCRIPTION

Figure 1:
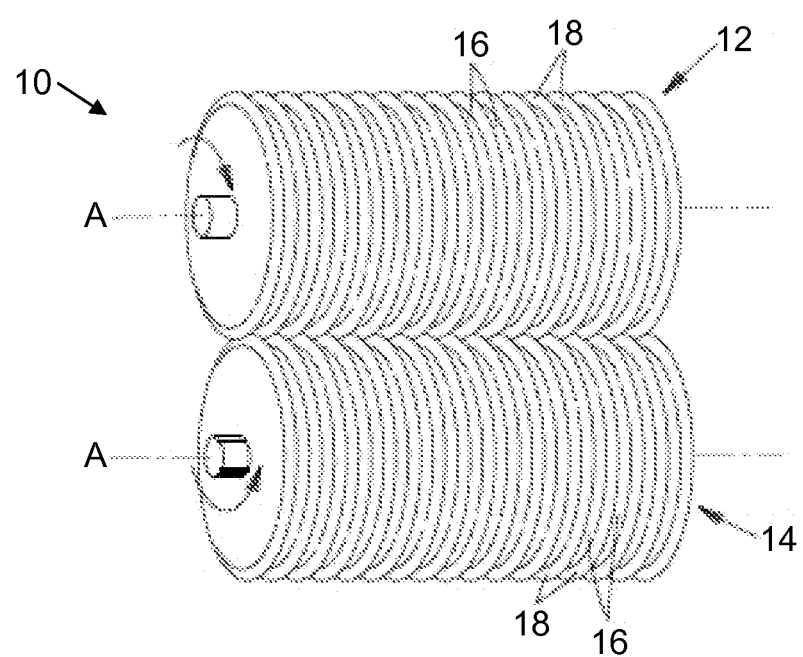
FIG. 1 is a perspective view of a prior art pair of ring rolls for deforming a web.

The following text sets forth a broad description of numerous different embodiments of the present invention. The description is to be construed as exemplary only and does not describe every possible embodiment since describing every possible embodiment would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

The present invention enables an apertured web which is stronger in the cross-machine direction so it doesn't easily tear in the cross-machine direction. A process for producing an apertured web having discrete, closely-spaced apertures with a desired, larger width in the cross-machine direction is described. The process can also produce a structure with alternating ridges and grooves, with apertures contained in the grooves. An apparatus that will allow a web to be apertured with desired, discrete, closely-spaced, larger-width apertures in the cross-machine direction is also described.

As used herein, the term "absorbent article" includes disposable articles such as sanitary napkins, panty liners, tampons, interlabial devices, wound dressings, diapers, adult incontinence articles, wipes, and the like. Still further, the absorbent members produced by the processes and apparatuses disclosed herein can find utility in other webs such as scouring pads, dry-mop pads (such as SWIFFER® pads), and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet.

As used herein, the term "absorbent member" refers to the components of the absorbent article that typically provide one or more liquid handling functionality, e.g., liquid acquisition, liquid distribution, liquid transportation, liquid storage, etc. If the absorbent member comprises an absorbent core component, the absorbent member can comprise the entire absorbent core or only a portion of the absorbent core.

As used herein, the term "aperture" refers to a hole. The apertures can either be punched cleanly through the web so that the material surrounding the aperture lies in the same plane as the web prior to the formation of the aperture (a "two dimensional" aperture), or holes formed in which at least some of the material surrounding the opening is pushed out of the plane of the web. In the latter case, the apertures may resemble a "three dimensional" aperture. Three dimensional apertures generally maintain more open area under an applied load. As used herein, the term "apertured" refers to a web comprising a plurality of apertures.

As used herein, the term "component" of an absorbent article refers to an individual constituent of an absorbent article, such as a topsheet, acquisition layer, liquid handling layer, absorbent core or layers of absorbent cores, backsheets, and barriers such as barrier layers and barrier cuffs.

As used herein, the terms "corrugated" or "corrugation" mean a three-dimensional web topography comprising a plurality of generally parallel alternating ridges and grooves, wherein the ridges and grooves undulate about an axis X (drawn horizontally through a cross-section of the web). The ridges and grooves may undulate equally on either side of the axis, or may be lopsided.

As used herein, the term "cross-machine direction", "cross direction", or "CD" means the path that is perpendicular to the machine direction in the plane of the web.

As used herein, the term "deformable material" is a material which is capable of changing its shape or density in response to applied stresses or strains.

As used herein, the term "depth of engagement" ("DOE") means a degree of meshing between two rolls. The distance is measured from the outermost tip of the tooth or ridges on a first roll to the outermost tip of the tooth or ridges on a second roll. The terms "meshing" or "intermeshing," as used herein, refer to arrangements when the teeth/ridges on one of the rolls extends toward the surface of the other roll and at least some of the teeth/ridges have portions that extend between and below an imaginary plane drawn though the tips of the teeth/ridges on the surface of the other roll.

As used herein, the term "discrete" means distinct or unconnected. When the term "discrete" is used relative to teeth on a raised ridge roll, it is meant that the distal (or radially outwardmost) ends of the teeth are distinct or unconnected in all directions, including in the machine and cross-machine directions (even though bases of the teeth may be formed into the same surface of a roll, for example). For example, the ridges on a ring roll are not considered to be discrete.

As used herein, the term "disposable" describes absorbent articles and other products which are not intended to be laundered or otherwise restored or reused as an absorbent article or product (i.e., they are intended to be discarded after use and, preferably, to be recycled, composted or otherwise disposed of in an environmentally compatible manner).

As used herein, the term "hollow" describes ridges and grooves present in a web made by the apparatuses and processes described herein; the ridges and grooves comprise open spaces having no web material present. For instance, a web comprises ridges, grooves, and an X axis drawn horizontally through a cross-section of the web; the area above the X axis but under the top of the ridge is hollow, or comprises a hollow area. Likewise, the area below the X axis but above the bottom of the groove is hollow, or comprises a hollow area.

As used herein, the term "machine direction" or "MD" means the path that material, such as a web, follows through a manufacturing process.

As used herein, the term "macroscopic" refers to structural features or elements that are readily visible and distinctly discernible to a human having 20/20 vision when the perpendicular distance between the viewer's eye and the web is about 12 inches (30 cm). Conversely, as used herein, the term "microscopic" refers to such features that are not readily visible and distinctly discernible under such conditions.

As used herein, the terms "ring roll" or "ring rolling" refer to a process using deformation members comprising counter rotating rolls, intermeshing belts, or intermeshing plates containing at least portions of continuous ridges and grooves where intermeshing ridges (or projections) and grooves (or recesses) of deformation members engage and stretch a web interposed therebetween. Unless otherwise stated, ring rolls alone do not aperture webs. For ring rolling, the deformation members can be arranged to stretch the web in the cross machine direction, the machine direction, or in a helical direction/at an angle to the CD or MD depending on the orientation of the ridges and grooves. Examples described herein which pertain to one direction are to be understood as enabling the non-described directions.

As used herein, the term "rotary knife aperturing" (RKA) refers to a process and apparatus using intermeshing deformation members, or rolls, wherein one or more roll comprises a plurality of teeth. The teeth can be sharpened to cut through as well as deform a web to produce an apertured web, or in some cases, a three-dimensionally apertured web, as disclosed in US 2005/0064136A1 and US 2006/0087053A1.

The terms "SELF" or "SELF'ing", refer to Procter & Gamble technology in which SELF stands for Structural Elastic Like Film. Processes, apparatus, and patterns produced via SELF are illustrated and described in U.S. Pat. Nos. 5,518,801; 5,691,035; 5,723,087; 5,891,544; 5,916,663; 6,027,483; and 7,527,615 B2. While the process was originally developed using tooth geometries that would deform a polymer film without producing apertures, other tooth geometries have been developed that are more conducive to forming tufts (in the case of a nonwoven) or tents (in the case of a film) with apertures on the leading and trailing ends. A process using SELF'ing to form tufts with apertures in a nonwoven web is disclosed in U.S. Pat. No. 7,682,686 B2.

As used herein, the term "teeth" refers to any elements on the surface of a roll that are capable of aperturing a web.

I. Apertured Web Materials

While the term "apertured web materials" is utilized herein, the object is to create components, such as absorbent members (or non-absorbent members), for absorbent articles from such apertured web materials. In such cases, the apertured web materials will be cut into individual components for absorbent articles (such as topsheets, backsheets, acquisition layers, absorbent cores). In the case of webs used in absorbent articles, such new structures may include those that provide improved properties (such as improved softness, fluid handling, or other properties) in a predetermined portion of the web. These apertured webs can be cut to form various other components of products for packaging (e.g., flow wrap, shrink wrap, and polybags), wipes, facial tissue, toilet tissue, paper towels, and the like.

Discrete, closely-spaced apertures having a larger width in the CD direction can be provided in webs and the components formed therefrom which are not possible to produce with current methods and tooling. The new apertures comprise greater open areas and lower aspect ratios (aperture length: aperture width) which (in the case of a film) result in increased web strength, as compared to equivalent open area apertures achievable via the prior art (see FIG. 2D).

In addition, webs created with this new technology have a unique, more textured appearance. The textured webs may comprise alternating ridges and grooves, wherein apertures are intentionally contained within the grooves. In the case of the apertured webs being used for absorbent articles, the web may offer better fluid acquisition, breathability, or separation from the body, thus promoting a drier, cleaner feeling. For example, in a sanitary napkin, apertures located in grooves help channel and transfer fluid from a topsheet to lower absorbent members. Not only do the apertures provide these benefits, but any corrugation present in the final web may additionally support these benefits. For instance, the corrugation offers at least partial non-contact with the body, which improves breathability, produces a drier feel, and promotes less contact with a wet/soiled surface which may irritate skin or feel uncomfortable. In the case of a sanitary napkin, corrugations may channel fluid in a longitudinal direction along the sanitary napkin and keep fluid away from the side edges of the sanitary napkin.

The web (or "precursor web") that will be apertured can comprise any suitable deformable material, such as a woven, nonwoven, film, flat film, micro-textured film, combination, or laminate of any of the foregoing materials. As used herein, the term "nonwoven web" refers to a web having a structure of individual fibers or threads which are interlaid, but not in a repeating pattern as in a woven or knitted fabric, which do not typically have randomly oriented fibers. Nonwoven webs may or may not comprise thermal bond points. This may include paper substrates, such as tissue, drylap, liner board, filter paper, and combinations thereof. Nonwoven webs or fabrics have been formed from many processes, such as, for example, meltblowing, spunbonding, hydroentangling, airlaid, wetlaid, through-air-dried paper making processes, and bonded carded web processes, including carded thermal bonding. Depending on the forming process, the nonwoven web may or may not comprise thermal bond points. Film materials can be single layer, multi-layer, embossed, or micro-textured. The woven, nonwoven, film, combination, or laminate can be made of any suitable materials including, but not limited to natural materials, synthetic materials, and combinations thereof. Suitable natural materials include, but are not limited to cellulose, cotton linters, bagasse, wool fibers, silk fibers, etc. In some embodiments, the web materials may be substantially free of cellulose, and/or exclude paper materials. In other embodiments, the processes described herein may be performed on cellulose-containing precursor materials. Suitable synthetic materials include, but are not limited to rayon and polymeric materials. Suitable polymeric materials include, but are not limited to: polyethylene (PE) (e.g., linear low density polyethylene (LLDPE), low density polyethylene (LDPE), high density polyethylene (HDPE), or the like), polyester, polyethylene terephthalate (PET), and polypropylene (PP). Any of the materials described above may comprise post-consumer recycled material. The apparatuses described herein work with a wide range of materials and lower cost materials. For instance, one can use commodity spunbond nonwovens, multiple layers with different chemical & mechanical properties and control the degree of inter-mixing of the two or more layers, nonwovens with various fiber formulations & formations; or films. In addition, this apparatus can run directly on-line (and not lose loft due to roll compression/storage).

Various polymers can be used to produce the webs of interest. Potential materials include biopolymers made from non-petroleum sources such as bio-derived polyethylene (bio-PE), bio-derived polypropylene (bio-PP), bio-derived polyethylene terephthalate (bio-PET), and bio-derived poly (ethylene-2,5-furandicarboxylate) (bio-PEF). These materials can be partially or completely derived from at least one renewable resource where a renewable resource refers to a natural resource that can be replenished within a 100 year time frame. Renewable resources include plants, animals, fish, bacteria, fungi, and forestry products and may be naturally occurring, hybrids, or genetically engineered organisms. Natural resources such as crude oil, coal, and peat which take longer than 100 years to form are not considered to be renewable resources. Other polymers derived from non-petroleum sources include starch-based polymers and cellulosics. Additionally, recycled resins such as post-consumer regrind r-HDPE, r-LLDPE, r-LDPE, r-PET, r-PEF, or r-PP can be used at 100% or blended with various resins. Polymers derived from renewable resources and recycled resins could be used on their own, or blended into petroleum-based polymers at varying levels in order to control the cost. Sources and methods of making polymers from non-petroleum sources can be found in U.S. Pat. No. 8,063,064 B1 and US 2011/0319849 A1.

The present inventions are directed to apertured web materials and apparatuses and processes for aperturing and stretching a web to create such materials that overcome one or more of the shortcomings of the prior art. Stretching, or growing, a web is beneficial because it enables lower costs via overall basis weight reduction of the web. By aperturing and then stretching in the same process step, a wider, more preferred aperture is created in the web material. Here, aperturing and stretching occurs in a single unit op in a registered manner so that the stretching occurs while the tooth is still penetrating the material and, therefore, doesn't allow the aperture to collapse when stretched. The additional stretching step not only allows an aperture to be wider, but also has the potential to create a web with a corrugated appearance. Such an aperturing-then-stretching combination must be exactly registered. If aperturing and stretching were in separate steps, like the prior art, the apertures wouldn't be registered with the stretching ring roll and the apertures may close up. Also, webs created with this new process are softer and more drapable from stretching (loosened and/or thinned fibers and/or films). Thinner webs are generally desirable because less fluid can be retained by the web. This is important when a web is used as a topsheet for an absorbent article, as there is less saturation in the topsheet.

In one non-limiting embodiment, the apertured web material comprises a web having discrete apertures formed therein. The web has a first surface and a second surface opposite the first surface. The web comprises substantially non-apertured regions, or lands, which surround a plurality of discrete apertures.

The apertures are densely packed within a relatively small area. For example, the center-to-center spacing in any direction between apertures may be less than or equal to about 20 mm, 10 mm, 5 mm, 3 mm, 2 mm, 1 mm, or 0.5 mm. The total number of apertures in an area that measures 1 square inch (645 mm$^2$) may be greater than or equal to 4, 25, 100, 250, 500, 1000, or 3000. The number of apertures in a one inch square area can be determined by marking a square area on the material that measures 1 inch (25.4 mm) by 1 inch with a fine tip pen or marker and counting the number of first, second, third, etc. apertures that lie fully or partially within and on the boundary of the 1 inch square. A low power microscope or other magnifying aid can be used to aid visibility of the apertures in the material if needed. The apertures may be of any suitable configuration.

The apertures may be of any suitable size. Typically, the apertures will be macroscopic. The plan view area of the apertures may be greater than or equal to about 0.5 mm$^2$, 1 mm$^2$, 5 mm$^2$, 10 mm$^2$, or 15 mm$^2$ The processes described herein can also be used to create apertures that are microscopic which have plan view areas less than 0.5 mm$^2$ In addition to apertures, the web may comprise alternating ridges and grooves, wherein the apertures are located in the grooves. The ridges may extend continuously or form discontinuous ridges in the deformed region of the web. The grooves may extend continuously with apertures spaced at regular intervals within the grooves. Note that if the web is turned upside-down, the grooves will become the ridges and the ridges will become grooves, and the apertures will now be in located in the ridges. The apertures may be two-dimensional or three-dimensional, depending on the process and material parameters. In the case of three-dimensional apertures, the base of the apertures will extend in the opposite direction of the ridges. The sides of the ridges and sides of the grooves are more oriented in the z-direction than the tops of the ridges and bottoms of the grooves.

In the case of a film, the sides of the ridges and the sides of the grooves may be thinner and have a lower basis weight than the tops of the ridges and the bottoms of the grooves as a result of the stretching process. This results in a web with alternating regions of higher caliper and basis weight, and regions of lower caliper and lower basis weight, with the higher caliper and basis weight regions being located in the tops of the ridges and bottoms of the grooves, and the regions with lower caliper and basis weight located in the sidewalls in-between. Alternating basis weight provides thinned/flexible areas for comfort and maintained thickness for strength.

In the case of a nonwoven, the basis weight is also decreased in the stretched areas, again resulting in a web with alternating regions of higher and lower basis weight, with the higher basis weight regions located in the tops of the ridges and bottoms of the grooves, and the lower basis weight regions located in the sidewalls in-between. In the case of a nonwoven, the web thickness may not decrease in the stretched areas because the fibers may detangle and move away from each other. However, the thickness of some of the individual fibers may decrease as a result of the stretching, resulting in fiber diameters that range from 40% to 80% of the original fiber diameter. The average fiber diameter at the tops of the ridges and the average fiber diameter at the bottoms of the grooves may be greater than the average fiber diameter at the sidewalls. While in tooth lock at the ridges and grooves, the base web thickness does not vary significantly. Although the web is textured, the thickness of the web locally at the ridges and grooves does not vary significantly as the ridges and grooves are not filled, rather they form hollow areas, because they have been deformed out of plane. Hollow ridges are not able to retain as much fluid as filled ridges, which can provide dryness benefits when used as a topsheet in an absorbent article. As a result of the stretching, the web permanently elongates in the direction of the stretching. Suitably, the web thickness in the stretched areas is from 20% to 80% of the original web thickness.

II. Prior Art Apparatuses for Deforming Web Materials

Prior art approaches are not suitable for creating apertures having wider dimensions in the cross-machine direction—particularly with tough or tear-resistant films. Therefore, it is desirable to design a process that enables aperturing and then stretching in the same process step (i.e., within the same nip and while the aperturing teeth are still penetrating the web) to obtain apertures in the web material which have larger dimensions in the cross-machine direction than are obtainable with the prior art approaches. Prior art approaches are also not suitable for creating webs having alternating ridges and grooves, with apertures located in the grooves, using high speed aperturing and stretching means such as that described here.

FIG. 1 shows a first prior art apparatus 10 in which the rolls 12 and 14 are referred to herein as ring rolls. The rolls 12, 14, as in the case of the rolls in the other apparatuses shown and described herein, are carried on respective rotatable shafts having their axes A of rotation disposed in a parallel relationship. In all of the embodiments described herein, the rolls are non-contacting, and axially-driven. In this embodiment, the surfaces of the rolls have a plurality of alternating grooves 16 and ridges 18 extending around the circumference of the rolls. In other embodiments, the ridges and grooves may extend parallel to the axes A of the rolls. One or more such rolls can be used in the various embodiments of the apparatuses described herein.

In the embodiment shown in FIG. 1, and the various other embodiments described herein, the rolls mesh or at least partially intermesh. As shown in FIG. 1, the rolls typically rotate in opposite directions (that is, the rolls are counter-rotating). This is also the case for the other embodiments described herein.

FIGS. 2A-2C show a second prior art apparatus 20 in which the top roll 22 is a Rotary Knife Aperturing (or "RKA") roll and the bottom roll 24 is referred to herein as a ring roll. The apparatus comprises a pair of counter-rotating, intermeshing rolls, wherein the top roll 22 comprises pyramidal teeth 30 having four or more sides, the sides being substantially triangular and being tapered from a base towards a tip, and the bottom roll 24 comprises circumferentially-extending grooves 26 and ridges 28. The teeth 30 are arranged in spaced apart circumferential rows with grooves therebetween. The teeth 30 extend from the top roll 22 at the base, and the base of the tooth has a cross-sectional length dimension greater than a cross-sectional width dimension. Typically, apertures are formed in a web material as the teeth 30 on the RKA roll 22 intermesh with grooves 26 on the ring roll 24. With respect to tooth height, tooth spacing, pitch, depth of engagement, and other processing parameters, RKA and the RKA apparatus can be the same as described in U.S. Patent Application Publication No. US 2006/0087053 A1.

The RKA roll 22 shown in FIG. 2A comprises a staggered (vs. standard) tooth pattern. As used herein, the term "staggered" means that adjacent teeth do not align in rows in the CD. As used herein, the term "standard" means that adjacent teeth align in rows in the CD and thus are non-staggered. As shown in FIG. 2C, the rolls 22 and 24 are aligned in the cross-machine direction such that the teeth 30 on the RKA roll 22 align with the grooves 26 on the ring roll 24. As the teeth 30 penetrate the web, the ridges on the mating ring roll 28 support the web such that the teeth 30 can penetrate the web and simultaneously form apertures in the opposite direction. FIG. 2D shows a top view of an exemplary prior art web 34 that can be made by an apparatus like that shown in FIGS. 2A-2C. The resultant web 34 comprises lands 36 surrounding apertures 38. Apertures 38 formed by prior art apparatuses like that of FIGS. 2A-2C comprise a length in the machine direction L and a width in the cross-machine direction W. These apertures are typically slit-like, having widths W much smaller than lengths L, particularly with tougher and more recoverable webs.

III. Apparatuses and Processes Employing a Roll with Teeth Extending from a Raised Ridge to Aperture Web Materials In general, the apparatus comprises two intermeshing forming structures that form a nip therebetween. Forming structures may comprise rollers, plates, belts, sleeves, other structures capable of imparting a texture to a web, or combinations thereof. The first forming structure comprises a plurality of first ridges and first grooves on the surface of the forming structure, wherein said first ridges have a top surface and said first grooves have a bottom surface. The first forming structure further comprises a plurality of spaced-apart teeth extending outwardly from the top surface of said first ridges, each tooth being capable of forming an aperture, wherein the top surface of said first ridge is located between the tips of said teeth and the bottom surface of said first grooves. A second forming structure comprises a plurality of continuous second ridges and second grooves.

More specifically, the apparatus comprises a single pair of counter-rotating, intermeshing rolls that form a single nip N therebetween. Although the apparatuses will be described herein for convenience primarily in terms of rolls, it should be understood that the description will be applicable to any suitable apparatus that may comprise any suitable type(s) of forming members, including, but not limited to: a pair of rolls; pairs of plates; conveyors with pucks (or small plates); belts; or combinations thereof. The first roll and second roll each comprise a surface 106, 108 which comprises a plurality of circumferentially-extending ridges and grooves. Alternatively, the ridges and grooves could extend in a direction parallel to the axis of the roll, as long as it is mated to a roll that has ridges and grooves extending in the same direction. The first roll additionally comprises a plurality of spaced-apart teeth, wherein the teeth extend outwardly from the top surfaces of the ridges. This creates a "raised ridge." The ridges of the second roll extend toward the axis of the first roll to a depth beyond the top of at least some of the ridges on the first roll. In this manner, the initial engagement of the tooth creates an aperture, which is then stretched in the cross-machine direction when the engagement proceeds to a depth below the raised ridge. By first aperturing, and then stretching in one process step, while the tooth is still penetrating the web, the resulting apertures have a larger width in the cross-machine direction than would apertures produced by a standard toothed roll as described above and shown in FIGS. 2A-2D.

The apertures of the present invention comprise lower aspect ratios (aperture length: aperture width) and much higher open areas than the apertures of the prior art, particularly when utilized with tougher films, e.g., those containing high levels of LLDPE. The new tooth geometry facilitates a high open area at lower tooling temperatures, enabling the formation of apertures in webs which could not be apertured with traditional tooth geometry. The new tooling geometry provides the ability to aperture webs at lower heats (e.g., between 35 and 70 degrees Celsius) or even at ambient temperatures rather than requiring the heating of the apparatus. Further, there are minimal to lower costs involved to create this tooling vs. prior tooling since, inter alia, less metal is removed. Accordingly, room temperature precursor webs may be used. In one embodiment, the precursor web and intermeshing rolls are not heated. Or, overall preheated webs may be used. Or, zoned preheating of webs may enable apertures in some zones and bubbles in others. Preheating may be accomplished by wrapping the RKA roll prior to engagement (with varying wrap times prior to engagement possible) or, by wrapping the ring roll prior to engagement. Likewise, heated or non-heated tooling may be used. Suitably, the web is heated by wrapping the RKA roll heated to 50-200 degC, or 50-100 degC. The RKA roll and ring roll may be driven at identical speeds of the outermost surface or there may be a speed differential between the two rolls.

The following figures show non-limiting examples of specific roll arrangements and the apertured web materials that can be formed thereby. These apparatuses are able to utilize a single nip, and run at higher processing speeds, with no heat in some cases, and at less expense than prior art methods for aperturing and stretching (e.g., since it is a simple mechanical process—just two intermeshing rolls).

FIGS. 3A and 3B show an exemplary apparatus 100 of the present invention which comprises a single pair of counter-rotating, intermeshing rolls 102, 104 that form a single nip N therebetween. The first (top) roll 102 is a variation of the RKA roll shown in FIG. 2A. This particular variation will be referred to herein as a "raised-ridge RKA roll." The second (bottom) roll 104 in the apparatus 100 shown in FIGS. 3A and 3B is a ring roll.

Figure 4A:
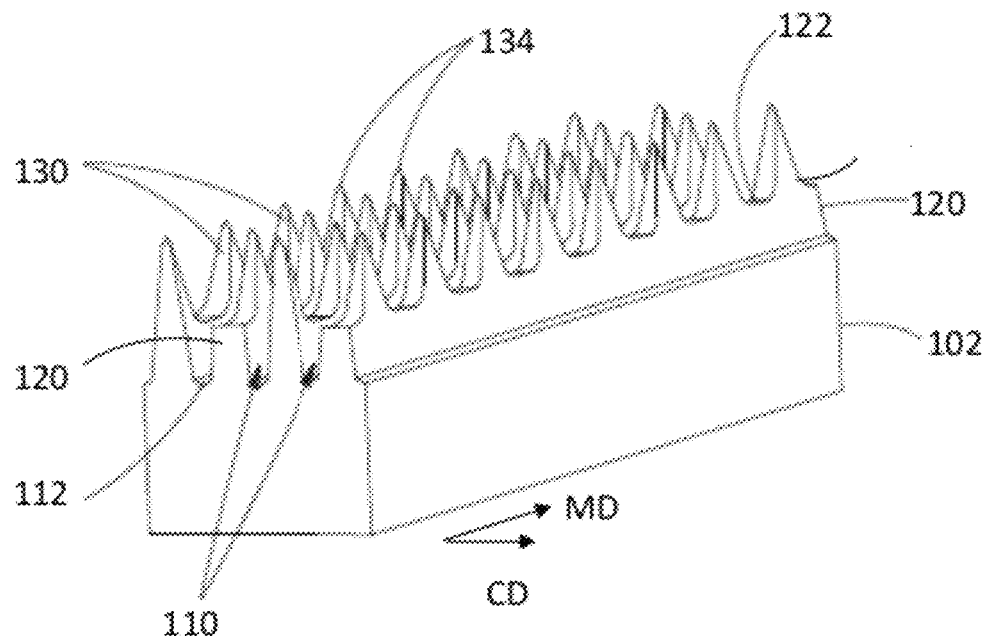
FIG. 4A is a perspective view of a portion of the surface of an exemplary raised ridge RKA roll.
Figure 4B:
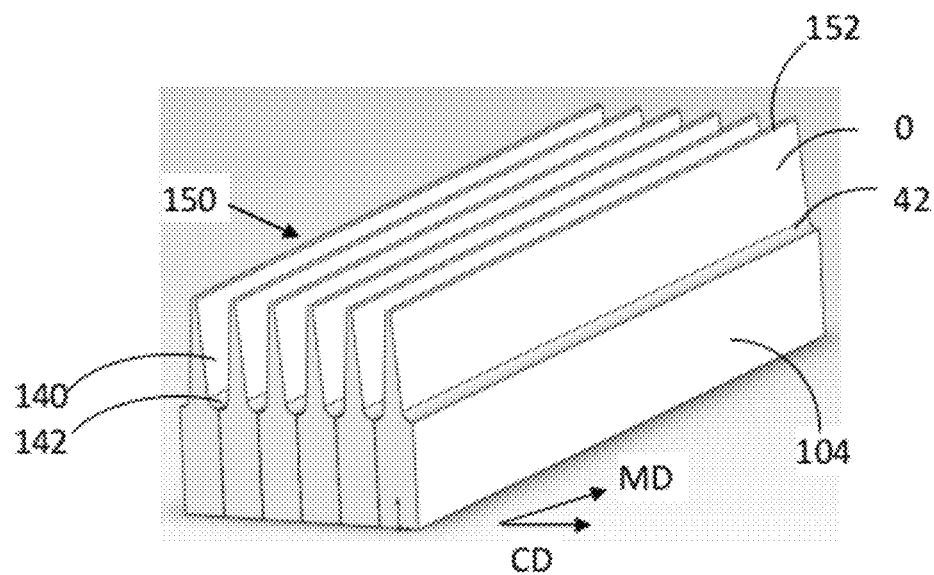
FIG. 4B is a perspective view of a portion of the surface of an exemplary ring roll.
Figure 4C:
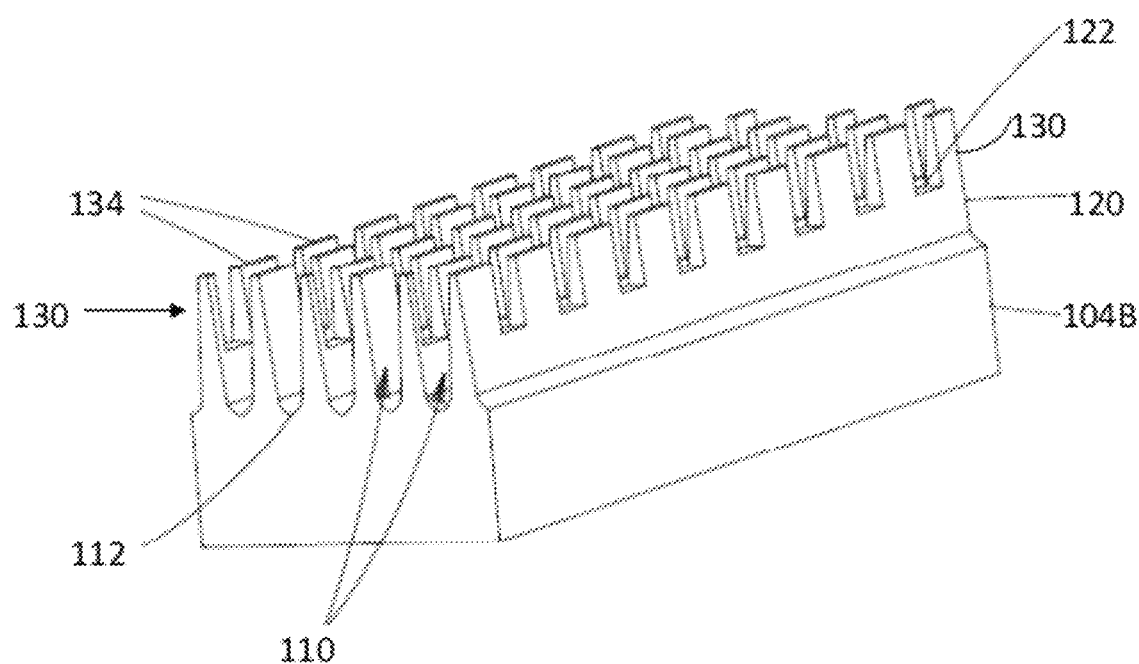
FIG. 4C is a perspective view of a portion of the surface of an exemplary raised ridge SELF roll.

As shown in FIG. 4A, the first roll 102 comprises a plurality of grooves 110 and ridges 120 and a plurality of staggered, spaced-apart teeth 130 extending outwardly from the top surface 122 of the ridges 120. The configuration of the roll 104 is such that the top surface 122 of the ridges 120 is disposed between the tips 134 of the teeth 130 and the bottom surface 112 of the grooves 110, directionally relative to the axis A of the roll. As shown in FIG. 4B, the second roll 104 comprises a plurality of grooves 140 and ridges 150. The grooves 140 have a bottom surface 142 and the ridges 150 have a top surface 152. Here, the distance between the top surfaces 152 of the ridges 150 and the bottom surfaces 142 of the grooves 140 is substantially the same around the circumference of the roll. FIG. 4C is an alternative second roll 104B in the form of a raised ridge staggered CD SELF roll. The configuration of the roll 104B is such that the top surface 122 of the ridges 120 is disposed between the tips 134 of the teeth 130 and the bottom surface 112 of the grooves 110, directionally relative to the axis A of the roll. Turning back to FIGS. 3A and 3B, the teeth 130 and ridges 120 of the first roll 102 extend toward the axis A of the second roll 104, intermeshing to a depth beyond the top 152 of at least some of the ridges 150 on the second roll 104.

Teeth suitable for this process must be conducive to aperturing webs. The teeth on the rolls may have any suitable configuration. A given tooth can have the same plan view length and width dimensions (such as a tooth with a circular or square shaped plan view). Alternatively, the tooth may have a length that is greater than its width (such as a tooth with a rectangular plan view), in which case, the tooth may have any suitable aspect ratio of its length to its width. Suitable configurations for the teeth include, but are not limited to:

teeth having a triangular-shaped side view; square or rectangular-shaped side view; columnar shaped; pyramid-shaped; teeth having plan view configurations including circular, oval, hour-glass shaped, star shaped, polygonal, and the like; and combinations thereof. Polygonal shapes include, but are not limited to rectangular, triangular, pentagonal, hexagonal, or trapezoidal. The side-walls of the teeth may taper at a constant angle from the base to the tip, or they may change angles. The teeth may taper towards a single point at the tooth tip, like that shown in FIG. 4A. The teeth can have tips that are rounded, flat or form a sharp point. Alternatively, the teeth may taper towards a multi-point, elongated tooth tip, like the SELF teeth shown in FIG. 4C. However, the tip of the tooth must form a sharp vertex with at least one of the vertical walls of the tooth (for example, the vertical walls on the leading and trailing ends of the teeth as shown in FIG. 4C), so the teeth aperture or puncture the web. In the case of the teeth shown in FIG. 4C, each tooth may form 2 apertures, one at the leading edge and one at the trailing edge of each tooth.

Figure 5A:
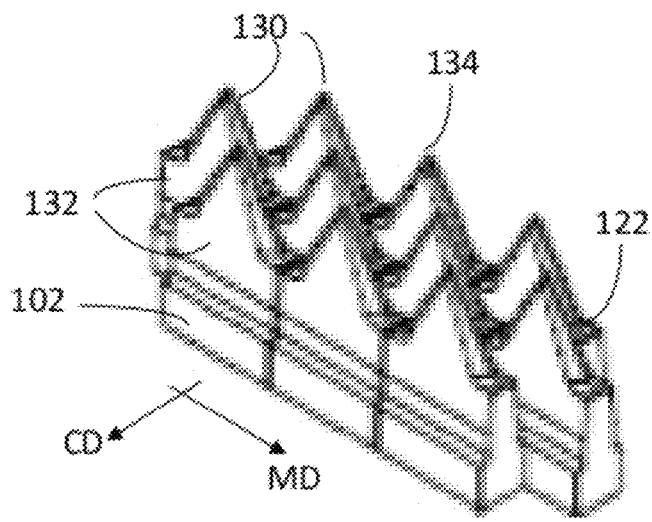
FIG. 5A is a perspective view of a portion of the surface of another exemplary raised ridge RKA roll.
Figure 5B:
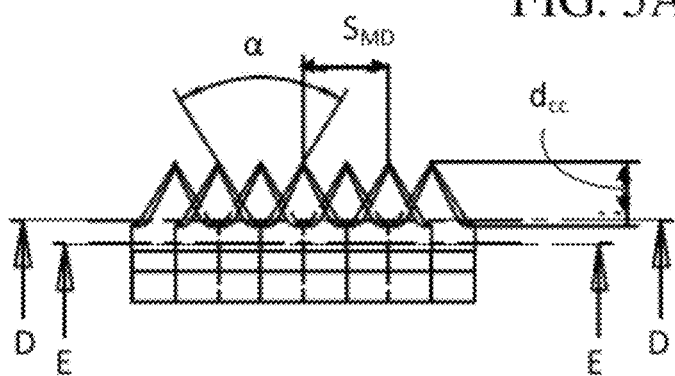
FIG. 5B is a side view of the tooth arrangement shown in FIG. 5A.
Figure 5C:
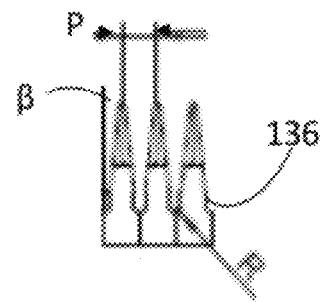
FIG. 5C is an end view of the tooth arrangement shown in FIG. 5A.
Figure 5D:
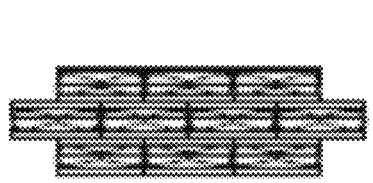
FIG. 5D is a top view of the tooth arrangement shown in FIG. 5A.
Figure 5E:
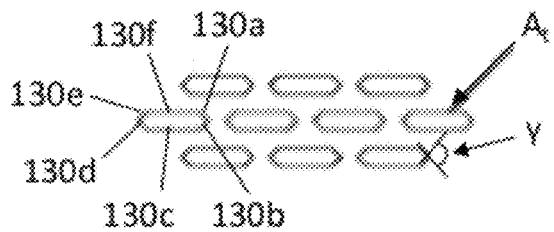
FIG. 5E is a section view along the line D-D of the tooth arrangement shown in FIG. 5B.
Figure 5F:
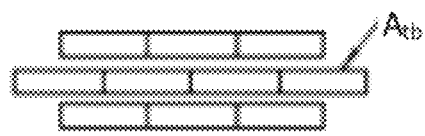
FIG. 5F is a section view along the line E-E of the tooth arrangement shown in FIG. 5B.

In one exemplary embodiment shown in FIGS. 5A-F, the first roll 102 comprises a plurality of pyramid-shaped teeth 130 extending outwardly from the top surface 122 of the ridges 120. FIG. 5A is a perspective view of a portion of the surface of another exemplary raised ridge RKA roll. FIG. 5B is a side view, FIG. 5C is an end view, and FIG. 5D is a top view of the tooth arrangement shown in FIG. 5A. FIG. 5E is a section view along the line D-D of the tooth arrangement shown in FIG. 5B. FIG. 5F is a section view along the line E-E of the tooth arrangement shown in FIG. 5B. The tooth cross-sectional area $A_t$ shown in FIG. 5E is less than the tooth cross-sectional area $A_{tb}$ shown in FIG. 5F. The sides (e.g., 130a-130f shown in FIG. 5E) are substantially triangular and tapered at a constant angle from a tip 134 to a base 132. The number of sides may be four (e.g., FIG. 4A), six (e.g., FIGS. 5A-6C), or another number less than or equal to twelve. The teeth 130 are arranged in spaced-apart circumferential rows with grooves 110 therebetween. The MD tip-to-tip tooth spacing $S_{MD}$ is from 0.4 mm to 15 mm (or from 3 mm to 8 mm). The CD pitch P is from 0.4 mm to 10 mm (or from 1 mm to 3 mm). The teeth have an included angle α of from 30 to 90 degrees (or from 45 to 65 degrees), a side wall angle β on the long side of the teeth (e.g., 130c, 130f) of from 3 to 15 degrees, and an end-facet included angle γ of the leading and trailing edges of the teeth (e.g., the angle between sides 130a and 130b or the angle between sides 130d and 130e) of from 45 to 120 degrees (or from 60 to 90 degrees). In some cases, the MD and CD tooth spacing, staggering, and included end-facet angle γ are chosen when the teeth are created by helical grinding.

There are different ways to finish the portion 136 where the teeth 130 and ridge surface 122 meet, for instance, truncated (FIG. 6A), wherein the taper on each side is cut off by a plane; semi-truncated (FIG. 6B), wherein the taper on at least one side is cut off by an arc; or non-truncated (FIG. 6C), wherein the taper on each side is not cut off in any manner. The teeth 130 shown in FIG. 6A taper from the tip 134 towards the base 132 and have a truncated lower portion 136. The taper and/or truncation may occur at different degrees. A truncated taper on a tooth makes the tooth easier to manufacture. In this case, referring to FIG. 7, the end facet angle γ and the ridge finishing can be accomplished in a single helical machining step as is well known in fabrication practices, by rotating the tooling in the circumferential direction $D_C$ while simultaneously advancing the machining in the axial direction of the tooling. The end facet of the tooth 130 will be created following the machining path $M_p$. For a tooth stagger $T_S$, the included end facet angle γ is thus created as 2*Arctan(CD Tooth Pitch "P"/Tooth Stagger "$T_S$").

The top surfaces 122 of the ridge between the teeth 130 may be finished in different manners. For instance, the surface 122 may be radiused or non-radiused. A radiused surface would protect the web from tears during forming, particularly in the case of a film, while a non-radiused surface (such as the surface 122 shown in FIGS. 6A-6C) may be more cost effective.

The configuration of the raised ridge RKA roll 102 is such that the top surface 122 of the ridges 120 are disposed between the tips 134 of the teeth 130 and the bottom surface 112 of the grooves 110, directionally relative to the axis A of the roll 102. The tooth height $h_t$ is defined as the distance between the tip 134 of the tooth 130 and the bottom surface 112 of the grooves 110. The tooth height $h_t$ is from 1 mm to 12 mm, or from 2 mm to 8 mm, or from 3 mm to 6 mm. The ridge height $h_r$ is at least 20%, typically from 20% to 95%, of the tooth height. The cross-cut depth $d_{cc}$ is defined as the distance between the tip 134 of the tooth 130 and the top surface 122 of the ridge 120. In this embodiment, the distance between the tip 134 of the tooth 130 and the top surface 122 of the ridge 120 is substantially the same around the circumference of the roll. The cross-cut depth $d_{cc}$ depends on the amount of deformation that is required to form the apertures. For example, the cross-cut depth $d_{cc}$ may be within the range of 0.2 mm to 9 mm, or from 1.0 mm to 4.0 mm or from 2.0 mm to 3.5 mm A smaller cross-cut depth $d_{cc}$ (at the same DOE) creates a more open aperture. The depth of engagement of the pair of rolls 102, 104 must be greater than the cross-cut depth $d_{cc}$. Suitably, the depth of engagement is at least 0.1 mm greater or 0.3 mm greater than the cross-cut depth. The DOE at the nip N is from 0.5 mm to 10 mm, or from 3 mm to 7 mm, or from 3 mm to 4 mm.

Figure 8:
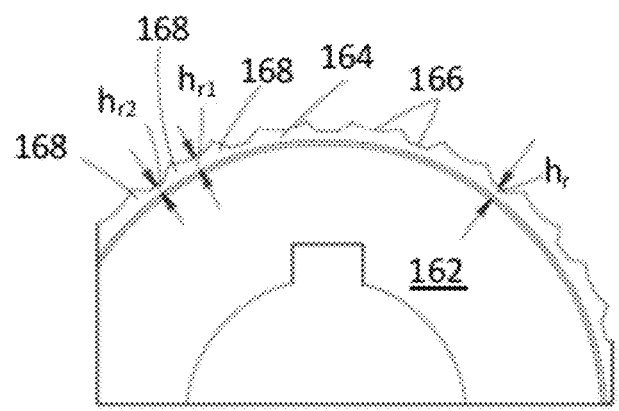
FIG. 8 is an enlarged side view of a portion of the surface of an alternative raised ridge RKA roll.

The ridge height $h_r$ is defined as the distance between the top surface 122 of the ridge 120 and the bottom surface 112 of the grooves 110. In some embodiments, such as shown in FIGS. 3B and 4A, the first roll 102 comprises a cross-direction width, and the distance between the top surfaces 122 of the ridges 120 and the bottom surfaces 112 of the grooves 110 is substantially the same around the circumference and across the CD width of the roll 102. Or, the distance between the top surfaces of the first ridges and the bottom surfaces of the second grooves can vary around the circumference or across the CD width of the first roll. Various alternative embodiments of the raised ridge rolls are possible. For example, as shown on roll 162 in FIG. 8, the height of the ridges $h_r$ may vary between at least some of the teeth 168. The ridge height $h_r$ depends on the amount of deformation that is required to form the desired apertures. The top surface 166 of at least one ridge 164 between a pair of teeth 168 will have a height $h_{r1}$ that is at least 10%, 20%, or 30% greater than the height $h_{r2}$ of another ridge 164 between another pair of pair of teeth 168. This roll 162 could be used in a process such as that shown in FIG. 3A in place of the raised-ridge RKA roll 102. The second roll may be a ring roll with ridges of different heights in either the circumferential or axial directions.

Figure 9A:
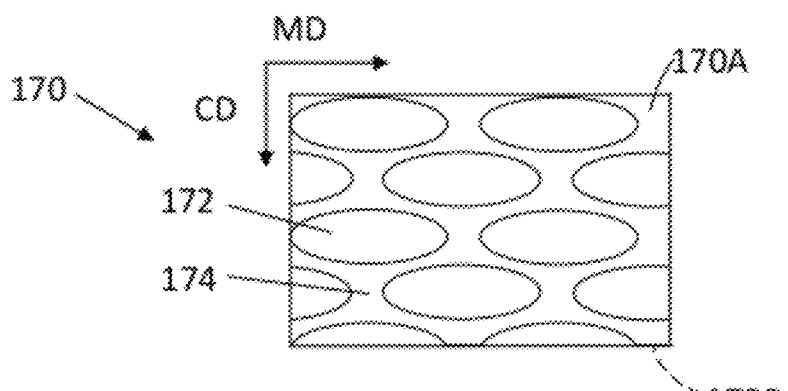
FIG. 9A is a top view of one example of a web that can be formed by using a variation of the rolls in FIG. 3A.

FIG. 9A shows an example of a web 170 which can be made by the apparatus shown in FIG. 3A: an RKA raised-ridge roll with a staggered tooth pattern for the upper roll 102 and a ring roll for the lower roll 104. The rolls 102 and 104 are aligned in the cross-machine direction such that the teeth 130 on the first roll 102 align with the grooves 140 on the second roll 104. As the teeth 130 on the first roll 102 penetrate the web 170, the ridges 120 between the teeth 130 on the RKA raised ridge roll 102 support the web 170 such that the ridges 150 on the second roll 104 can stretch the web 170 in the cross-machine direction.

Figure 9B:
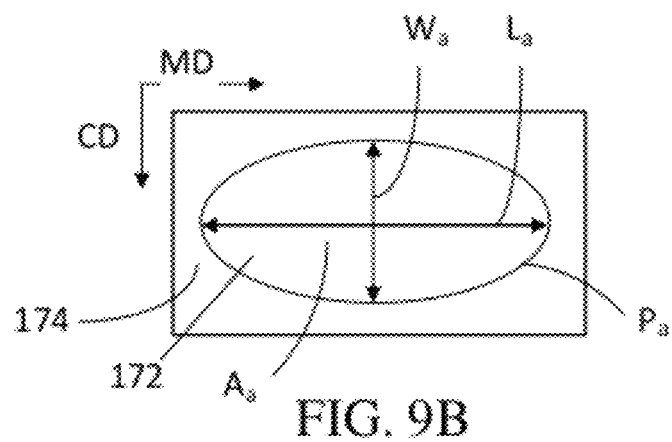
FIG. 9B is an enlarged view of one of the apertures shown in FIG. 9A.

The web in its initial state can be thought of as being relatively flat, and comprised entirely of non-apertured regions. The web 170 has a first surface 170A and a second surface 170B. When the web is fed in the machine direction into the nip N between the rolls (e.g., those shown in FIG. 3A), the web is: (i) apertured by the teeth 130 of the first roll 102 to form a plurality of spaced apart apertures 172; and (ii) stretched by the ridges 120 of the first roll 102 to stretch the apertures 172 in the cross-machine direction. As shown in the FIG. 9A web top view, the result is an apertured web 170 comprising apertures 172 and lands 174 surrounding the apertures 172. The apertures 172 may be pushed out of the plane of the web 160 in one direction (downward as viewed in FIG. 9A) thus the aperture 172 may have a height $H_a$. The apertures 172 are aligned in rows in the MD and the CD. FIG. 9B shows an enlarged top view of a single aperture 172. The apertures 172 comprise a length in the machine direction $L_a$ and a width in the cross-machine direction $W_a$. The apertures will preferably have a length-divided-by-width aspect ratio AR of from 1 to 4, or from 1.25 to 3, or from 1.5 to 2.5, or from 1.6 to 2.3. The apertures 172 further comprise an individual open area $A_a$ and a perimeter surrounding the open area $P_a$. The apertured web comprises a total open area of from 5% to 25%, or from 9% to 21%, or from 10% to 16%, or from 14% to 20% of the total web area. The apertured film comprises a tear, or tensile, strength (per 25.4 mm) in the cross-machine direction in the range of 1.5 N to 5 N, 2 N to 4 N, 2.5 N to 4 N, 2.5 N to 3.5 N, or 2.7 N to 3.9 N. The apertured nonwoven comprises a tensile strength (per 25.4 mm) in the cross-machine direction in the range of 2 N to 20 N, or higher. In one example, a web comprises a machine direction orientation and a cross-machine direction orientation, wherein the apertures comprise a length in the machine direction and a width in the cross-machine direction, and wherein a plurality of apertures comprise a length-divided-by-width aspect ratio of 1 to 4.

In some embodiments, the stretching step described above not only increases the CD width of the aperture, but also creates alternating ridges and grooves, where the apertures are located in the grooves. The portion of the web that is in contact with the ridges on the two rolls friction locks on the tops of the ridges and is not stretched, while the web in-between the ridges is stretched out of plane. The portion of the web that is stretched out of plane becomes more oriented in the z-direction. As a result, a web with ridges and grooves may be formed, with the apertures located in the grooves. Note that if the web is turned upside-down, the grooves will become the ridges and the ridges will become grooves, and the apertures will now be in located in the ridges The fibers at the tops of the ridges and the fibers at the bottoms of the grooves may be more oriented in an X-Y plane than are the fibers at the sidewalls.

Figure 11:
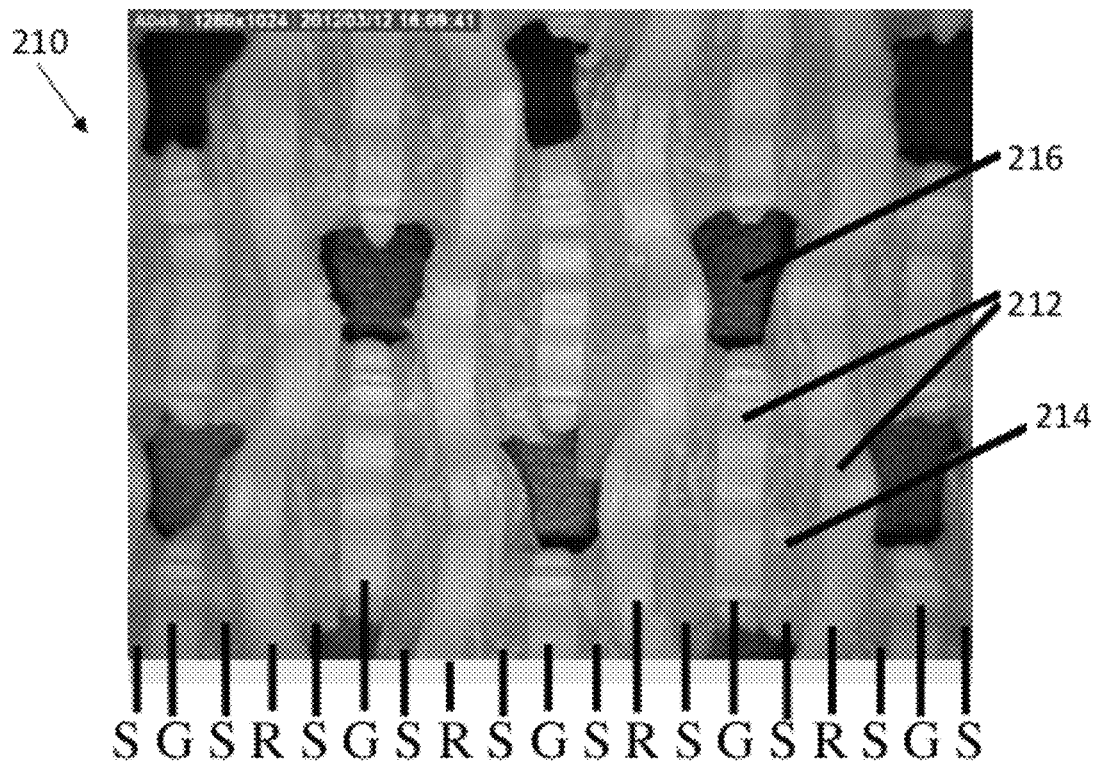
FIG. 11 is a top view of a 25 gsm PE film web (film is stretched/flattened out to show high and low basis weight regions).

In the case of a film, the web is thinned and the basis weight is decreased in the stretched regions, while the web thickness and basis weight are maintained in the regions of the web that are friction locked on the ridges of the rolls. This results in a web with alternating regions of higher and lower caliper, and alternating regions of higher and lower basis weight, with the higher caliper and higher basis weight regions being located in the tops of the ridges and bottoms of the grooves, and the regions with lower caliper and lower basis weight located in the sidewalls in-between. FIG. 11 is a top view of a 25 gsm PE film web 210 (film is stretched/flattened out to show high basis weight regions 212 and low basis weight regions 214).

Web 210 further shows ridges R, grooves G, and sidewalls S. Apertures 216 are present in the grooves G. As apparent, the high basis weight regions 212 are located in the ridges R and grooves G, whereas the low basis weight regions 214 are located in the sidewalls S.

Figure 12:
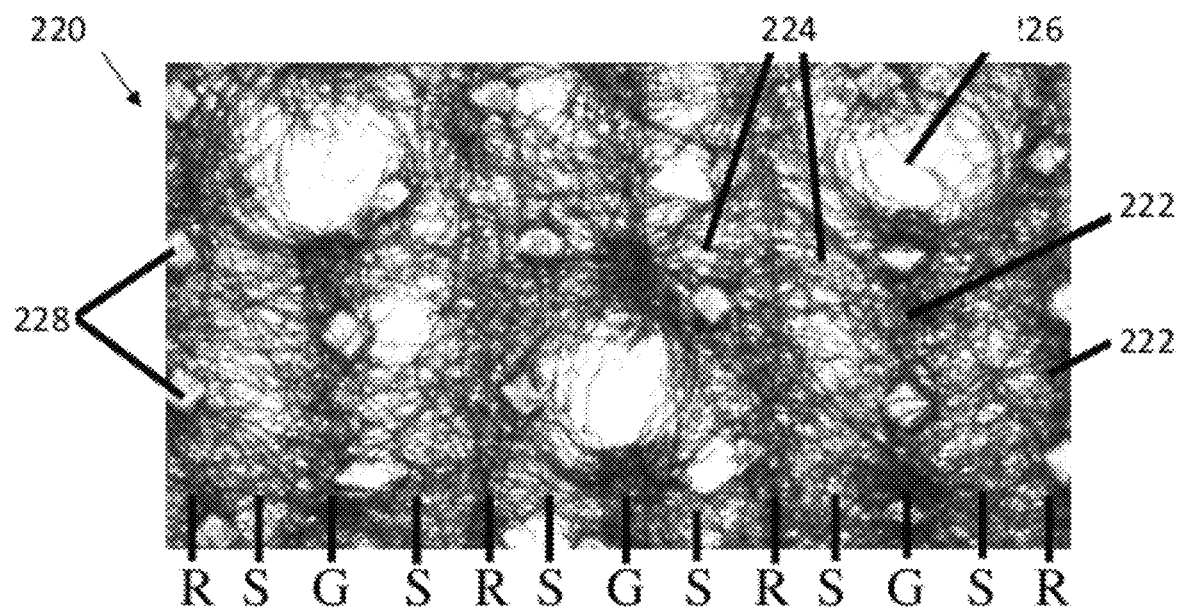
FIG. 12 is a top view of a 60 gsm PP nonwoven web (nonwoven is stretched/flattened out to show high and low basis weight regions).

In the case of a nonwoven, the basis weight is also decreased in the stretched areas, again resulting in a web with alternating regions of higher and lower basis weight, with the higher basis weight regions located in the tops of the ridges and bottoms of the grooves, and the lower basis weight regions located in the sidewalls in-between. FIG. 12 is a top view of a 60 gsm polypropylene nonwoven web 220 (nonwoven is stretched/flattened out to show high basis weight regions 222, and low basis weight regions 224). Web 220 further shows ridges R, grooves G, and sidewalls S. Apertures 226 are present in the grooves G. Thermal or fusion bond points 228 may be present in various locations on the web 220. As apparent, the high basis weight regions 222 are located in the ridges R and grooves G, whereas the low basis weight regions 224 are located in the sidewalls S. In the case of a nonwoven, the web thickness may not decrease in the stretched regions because the fibers may detangle and move away from each other. However, the thickness of some of the individual fibers may decrease as a result of the stretching. Note that the "regions" of the web used to characterize basis weight exclude the apertures themselves.

As a result of the stretching, the web permanently elongates in the direction of the stretching. If the web remains in its corrugated state, the majority of the increased web width is taken up by the ridges and grooves that are formed in the web. Alternatively, tension could be applied to expand the web, which would result in a decrease in the height and frequency of the ridges and grooves, and decrease the web's overall basis weight. If desired, the web could be expanded such that ridges and grooves no longer exist, and the web is back to its flattened state. This deformation process may stretch or grow a web by 10%, by 15%, by 20%, by 25%, or more in the CD. The amount of permanent stretch and degree of formation of the ridges and grooves depends on the tooling geometry, process conditions and the properties of the materials. Typically this process will permanently stretch or grow a nonwoven web material further than a film material. For example, a web may grow from 165 mm to 190 mm in the CD. Suitably, the web has an initial web basis weight and the lower basis weight regions have a basis weight which is lower than the initial web basis weight.

Figure 13:
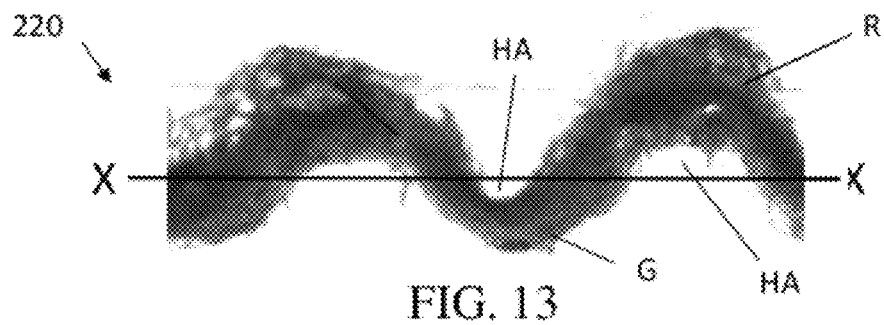
FIG. 13 is a cross-section view of the web shown in FIG. 12.
Figure 14:
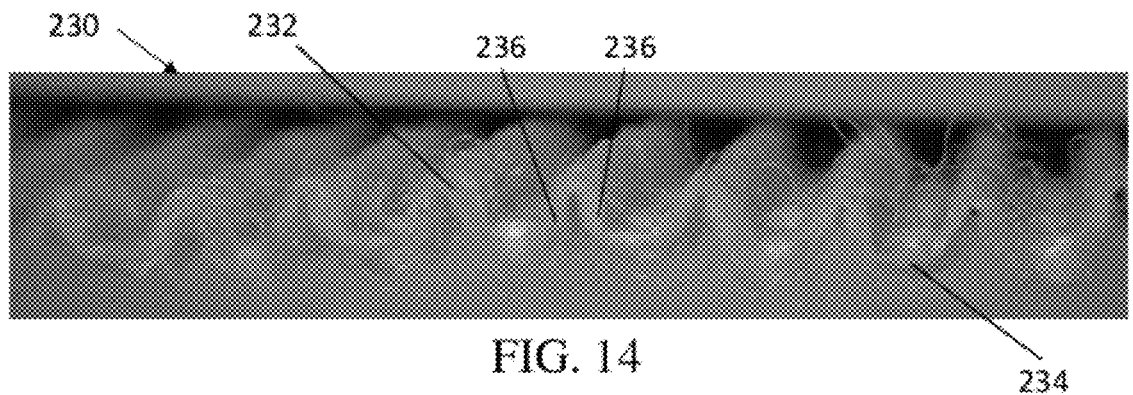
FIG. 14 is side perspective view of another nonwoven web.
Figure 15:
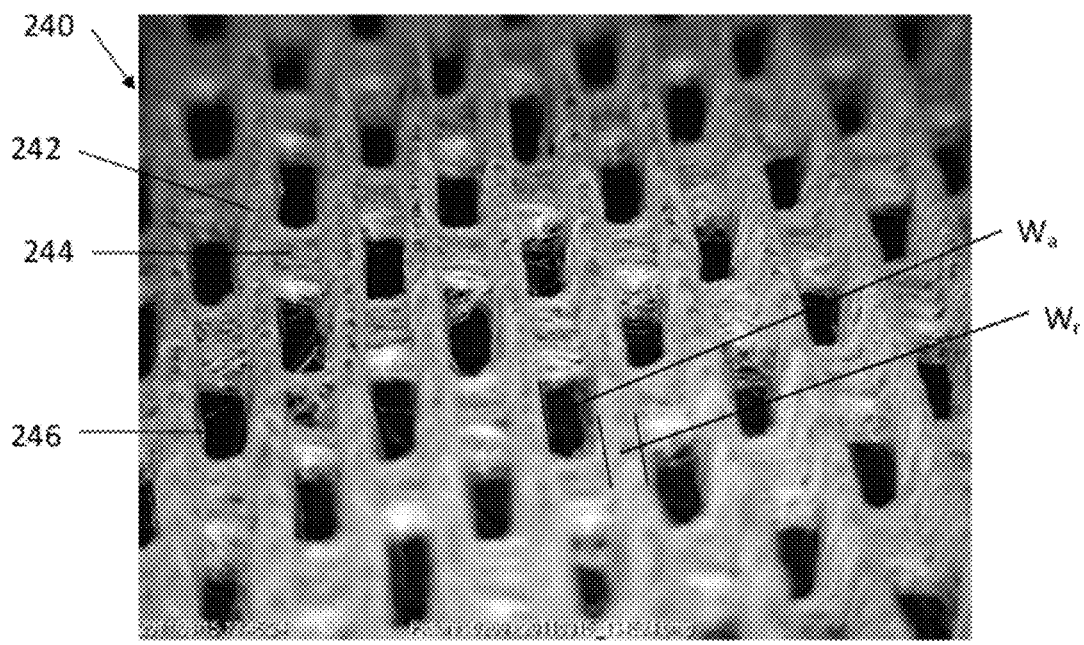
FIG. 15 is a top perspective view of a nonwoven web.
Figure 16:
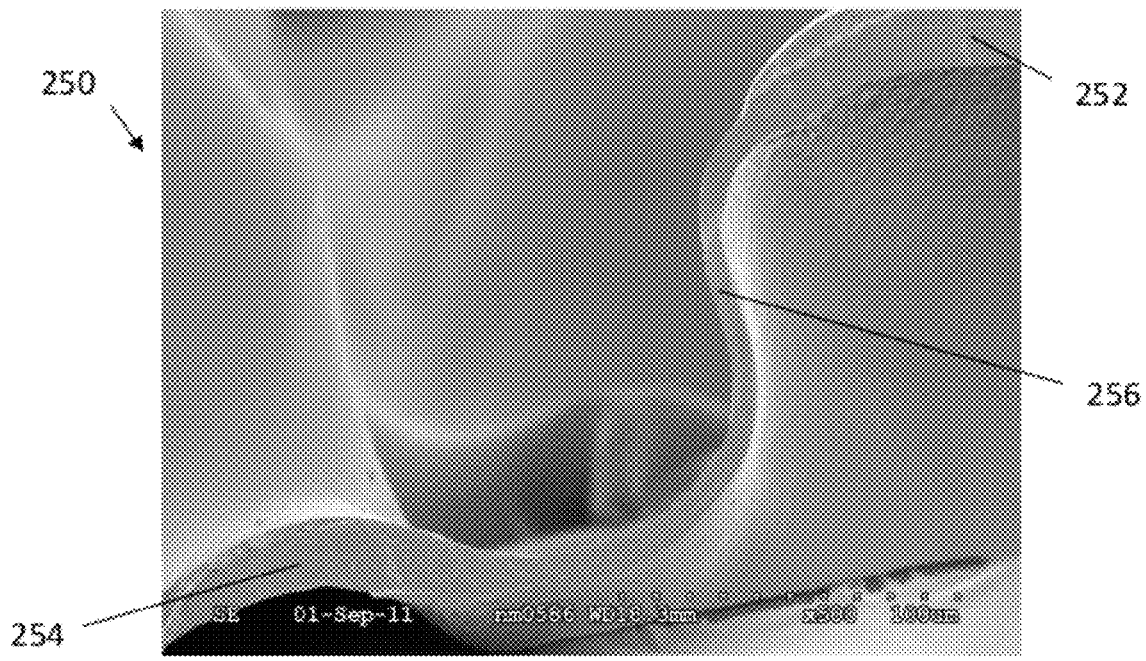
FIG. 16 is a cross-sectional view of a film web.

FIG. 13 is a cross-section view of the web 220 shown in FIG. 12 showing ridges R, grooves G, and axis X drawn horizontally through a cross-section of the web; the area above the X axis but under the top of the ridge is hollow, or comprises a hollow area HA. Likewise, the area below the X axis but above the bottom of the groove is hollow, or comprises a hollow area HA. Suitably, the web thickness at the tops of the ridges and the web thickness at the bottoms of the grooves are similar. The web thickness at the tops of the ridges and the web thickness at the bottoms of the grooves may be similar to the web thickness at the sidewalls. By similar, it is meant that the thicknesses are within about 60% of one another. Or, the web thickness at the tops of the ridges and the web thickness at the bottoms of the grooves is greater than the web thickness at the sidewalls. FIG. 14 is side perspective view of another nonwoven web 230 having ridges 232, grooves 234, and sidewalls 236. FIG. 15 is a top perspective view of 28 gsm polyethylene/polypropylene bico nonwoven web 240 comprising ridges 242 and grooves 244 and apertures 246 wherein the aperture width $W_a$ is greater than the ridge width $W_r$. FIG. 16 is a cross-sectional view of a film web 250 showing greater thinning at the sidewall 256 than at the top of the ridge 252 or bottom of the groove 254.

Figure 10:
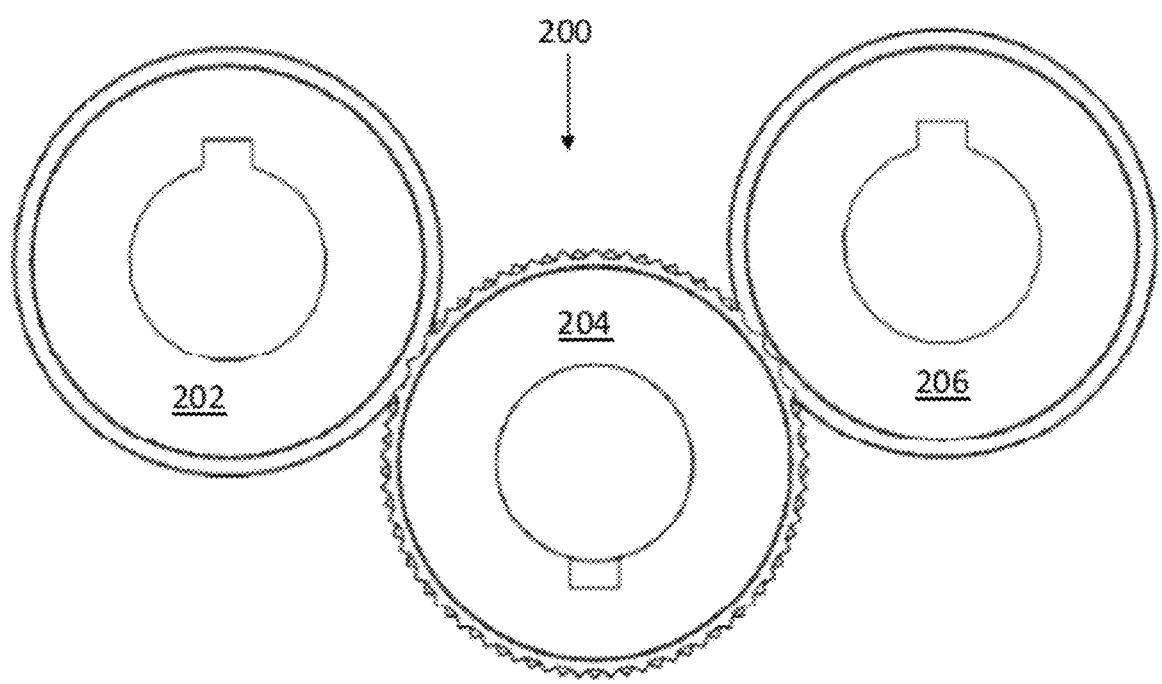
FIG. 10 is a side view of another embodiment of an apparatus for aperturing a web wherein the three rolls are in a planetary arrangement.

The processes of interest herein may also utilize multiple deformation steps in order to more gently deform the material or to impart a greater amount of permanent deformation. Such multiple deformation steps can be carried out by any suitable apparatuses described in U.S. patent application Ser. No. 13/094,195 to Lake, et al. Suitably, at least the first roll or the second roll also forms a nip with one or more additional rolls to thereby further stretch or deform the web. In one arrangement 200, as shown in FIG. 10, a ring roll 202 is mated to a raised-ridge roll 204 which is in turn mated to another ring roll 206 such that the rolls are in a planetary or satellite configuration. Processes utilizing multiple deformation steps may also be carried out on nested apparatuses having a relatively small number of rolls in a nested arrangement, or such apparatuses as the hybrid, closed loop, and shared bank with any suitable number of rolls in order to carry out the desired deformation.

Numerous alternative embodiments of the apertured web materials and processes of making the same are possible. For example, web materials can be provided which have different zones (including deformed zones and/or undeformed zones) across their surface with different features therein. The zones may by at least one feature selected from the group consisting of: ridge height, ridge spacing, aperture size, fiber diameter, film thickness, or combinations thereof. In one embodiment, an apertured web material can be provided which has zones of apertures, and in some cases, ridges and grooves. Webs disclosed herein may contain zones with different sizes of apertures and/or different sizes and frequencies of ridges and grooves. The web can comprise one or more layers. In another embodiment, the film is a micro-textured film comprising stretched areas and unstretched areas, wherein the stretched areas have micro-texture properties differing from the unstretched areas, and wherein the micro-textured properties are selected from the group consisting of open area, size, orientation, and combinations thereof. Webs made by the processes and apparatuses described herein may comprise ridges that run discontinuously across a deformed zone, or, ridges that run continuously across a deformed zone. To create such apertured web materials, the ring roll used may comprise zones of ridges and grooves. Or, the ring roll can have zones where the ridges are different heights, thereby creating differing depth of engagement (DOE), differing depth below the raised ridge, and thus apertures with differing widths and open areas. Alternatively or in addition, the raised ridge roll may comprise different zones, wherein ridge heights are different in different zones.

EXAMPLES

Example 1

Figure 6A:
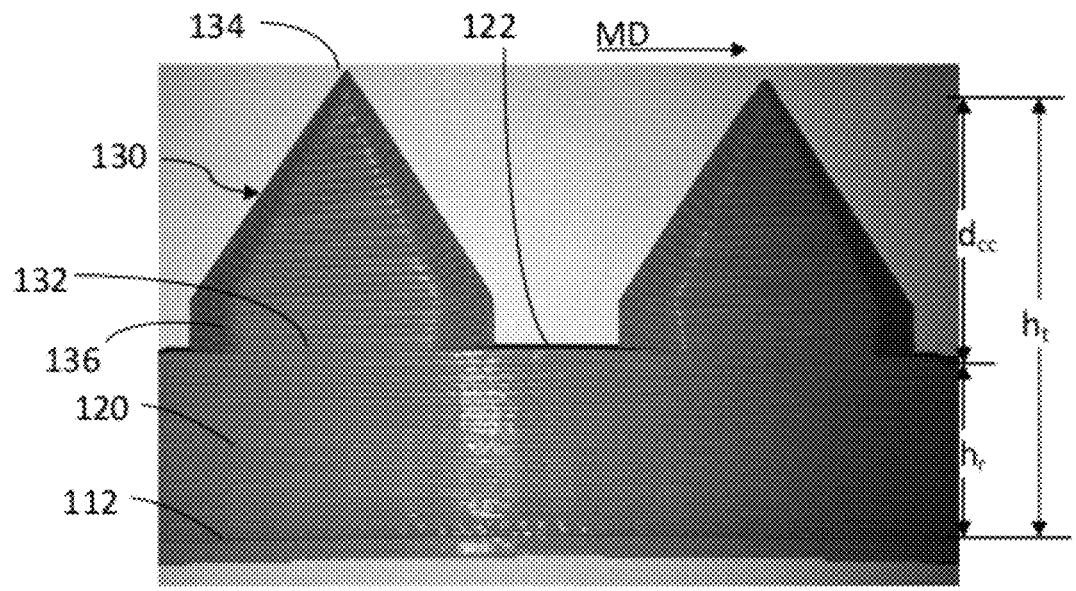
FIG. 6A is a front view of a first exemplary set of teeth, wherein the teeth are tapered and truncated.
Figure 6B:
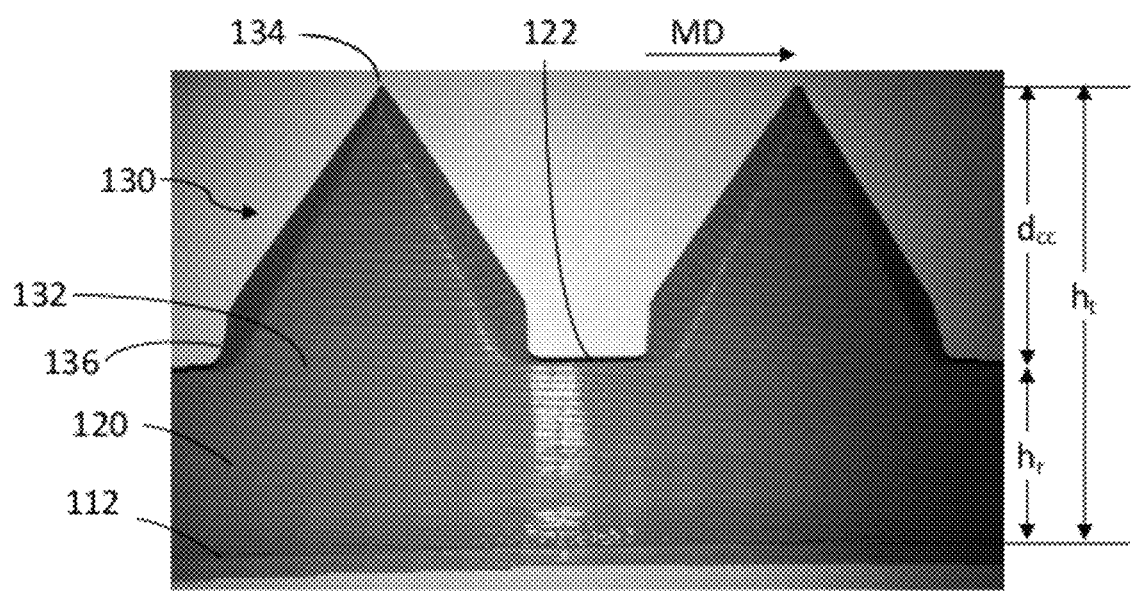
FIG. 6B is a front view of a second exemplary set of teeth, wherein the teeth are tapered and semi-truncated.
Figure 7:
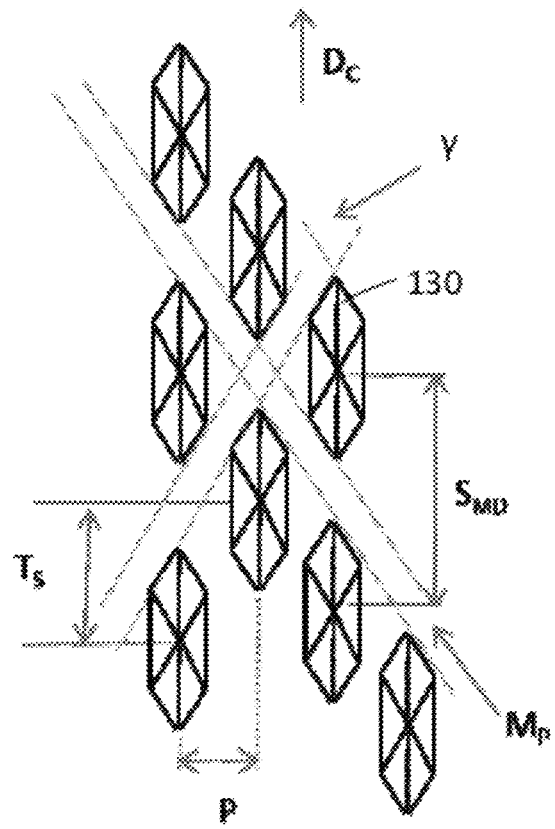
FIG. 7 is a schematic of a tooth pattern wherein the end facet angle γ and the ridge finishing can be accomplished in a single helical machining step.
Figure 17:
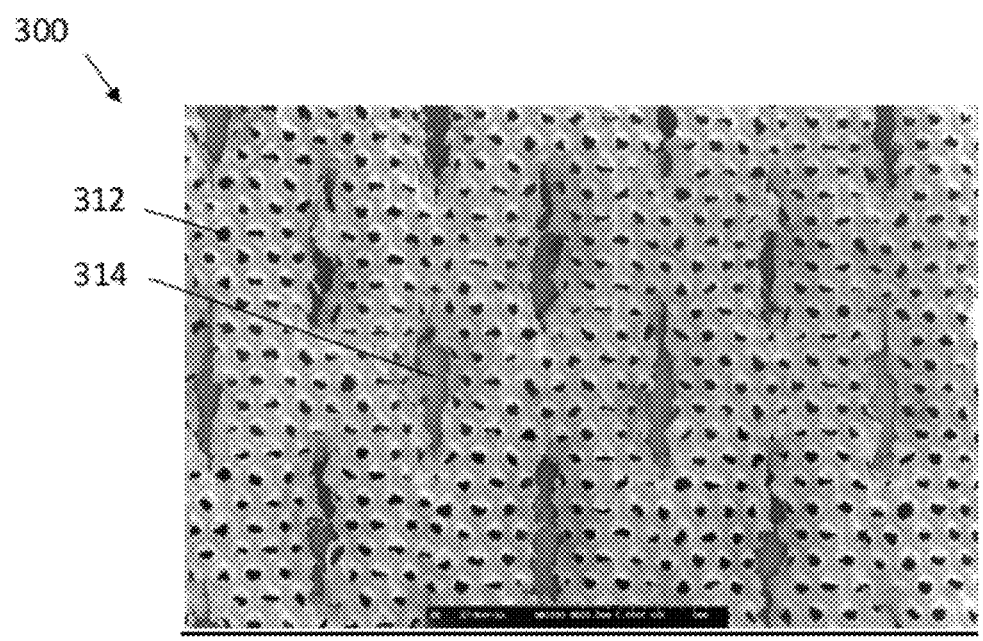
FIGS. 17, 18A, and 18B are top views of apertured film webs described in Example 1.

In one non-limiting example for making apertures in a polymer film, like the web 300 shown in FIG. 17 (comprising micro-apertures 312 and macro-apertures 314), an apparatus can be used that comprises a 1.5 mm pitch raised ridge RKA roll intermeshed with a 1.5 mm pitch ring roll at 3.8 mm depth of engagement. The raised ridge RKA roll has teeth that are oriented so the long direction runs in the MD. The teeth are arranged in a staggered pattern as shown in FIG. 5A. The teeth have a pyramidal shape with 6 sides that taper from the base to a sharp point at the tip, and have a height $h_t$ of 4.7 mm. The teeth have an included angle ($\alpha$ from FIG. 5B) of 62 degrees, a side wall angle on the long side of the tooth of about 6 degrees ($\beta$ from FIG. 5C), and an end facet included angle of 90 degrees ($\gamma$ from FIG. 5E). The ridges that span between the teeth on the RKA roll are non-radiused and form a flat surface. The teeth are finished at the ridge in a semi-truncated format as shown in FIG. 6B. The ridges and grooves extend circumferentially around the ring roll.

There are two different sections of teeth on the roll, which are exhibited to demonstrate the benefits of the raised ridge and referred to individually as "Section A" and "Section B". Section A has a MD tooth spacing $S_{MD}$ tip to tip of 4.9 mm, a cross cut depth ($d_{cc}$ in FIG. 6A) of 3.6 mm and resultant ridge height ($h_R$ in FIG. 6A) of 1.1 mm. Section B has a MD tooth spacing $S_{MD}$ tip to tip of 3.7 mm, a cross-cut depth $d_{cc}$ of 2.7 mm, and resultant ridge height $h_r$ of 2.0 mm.

The mating ring roll is 1.5 mm pitch with a height of 4.8 mm, a tip radius of 0.12 mm, and a side wall angle of about 4 degrees. Both rolls have a diameter of about 205 mm, and are heated to 80 degC. The RKA roll and ring roll are aligned in the CD such that the clearances on either side of the teeth are about equal.

The precursor web is a micro-apertured polymer film at a basis weight of 26 g/m², with a blend of LLDPE and LDPE, obtained from RKW-Group, Germany. LLDPE comprises about 60% of the film composition, LDPE about 30%, and inerts and fillers such as $TiO_2$ and the carrier resins thereof the remaining 10%. The micro-apertures are 55 mesh (apertures per inch in orthogonal directions), arranged in an equilateral triangle pattern with center-to-center spacings of about 462 microns. Aperture diameters are 175-200 microns and tapered cone heights of approximately 120 microns.

Figure 18A:
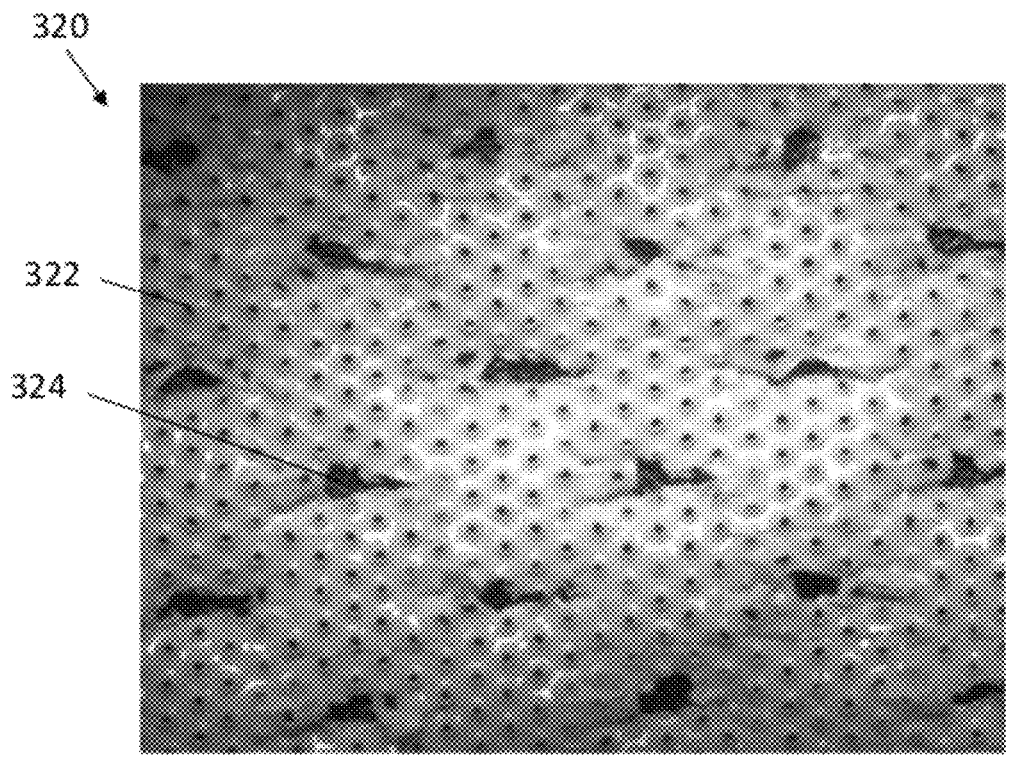
Figure 18B:
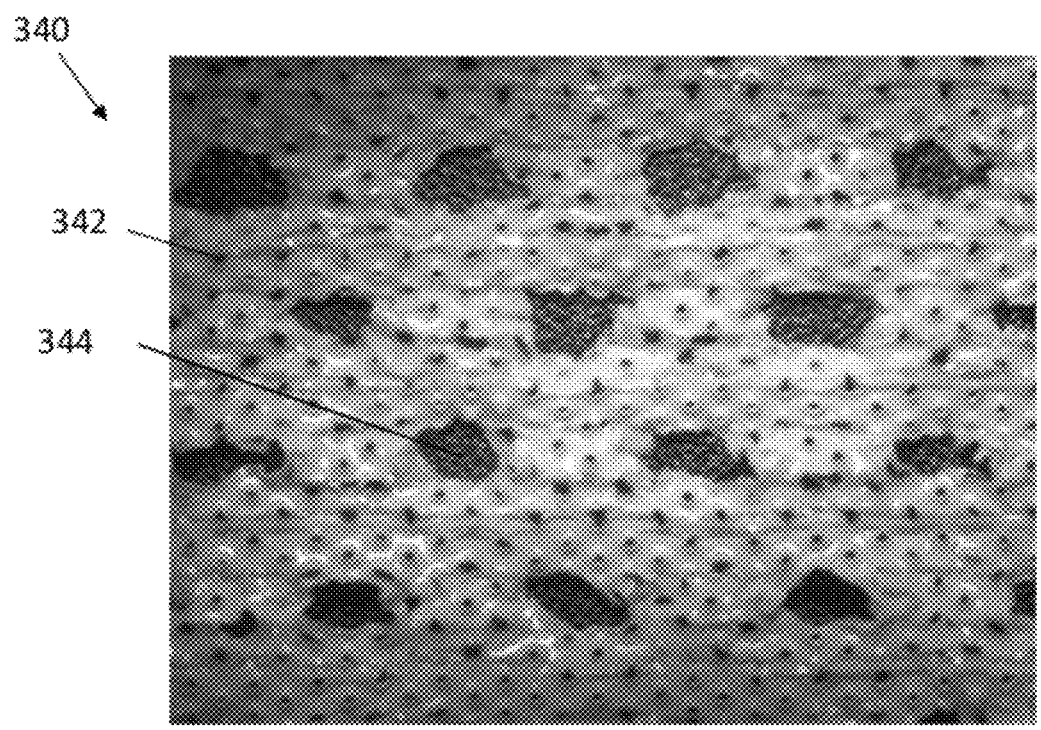

The precursor web is pre-wrapped on the ring roll prior to passing between the intermeshing rolls at a linear web speed of 480 meters/min. The micro-apertured cones side of the film is placed facing the RKA roll. A depth of engagement of 3.8 mm is used. The resultant films are shown in low magnification in FIGS. 18A and 18B. The open areas (% of film area with an open aperture), aperture lengths, and aperture widths of said films are measured with a vision system, such as can be purchased from Cognex Corporation of Natik, Mass., under the IN-SIGHT tradename. The open area, length and width comparison of apertures from Section A (FIG. 18A) vs. Section B (FIG. 18B) are shown in the table below. FIGS. 18A and 18B depict film webs 320, 340 having micro-apertures 322, 342 and apertures 324, 344.

|  | Cross-Cut Depth $d_{CC}$ (mm) | Raised Ridge Height $h_R$ (mm) | Open Area % | Aperture Length (mm) | Aperture Width (mm) |
|---|---|---|---|---|---|
| Section A | 3.6 | 1.1 | 5.76 | 1.20 | 0.52 |
| Section B | 2.7 | 2.0 | 14.63 | 1.40 | 0.63 |

Example 2

Figure 6C:
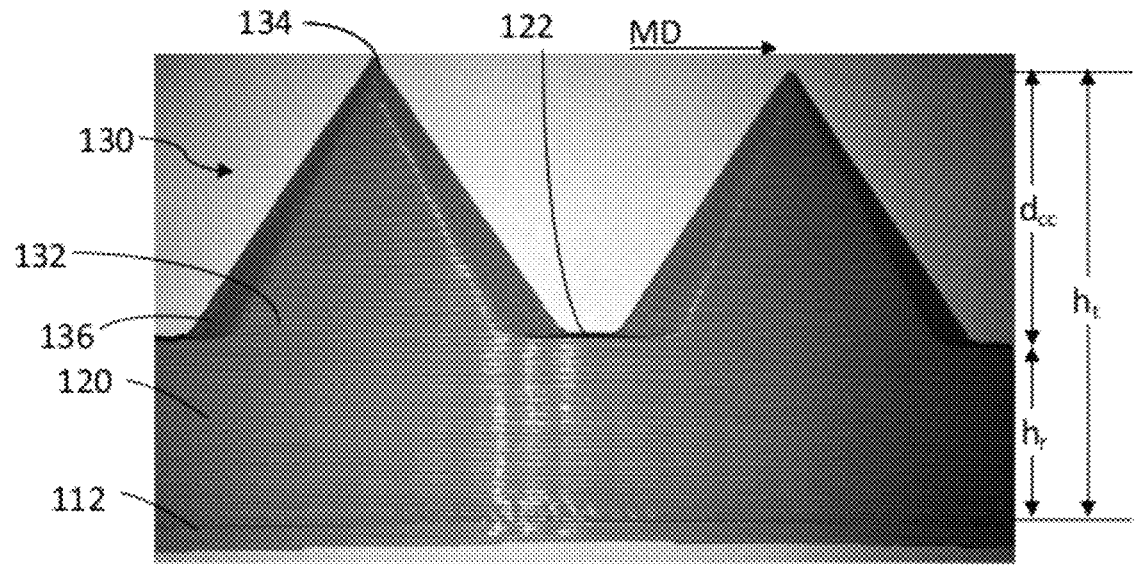
FIG. 6C is a front view of a second exemplary set of teeth, wherein the teeth are tapered and non-truncated.

In one non-limiting example for making a corrugated web having apertures in the grooves, an apparatus can be used that comprises a 2.0 mm pitch raised ridge RKA roll intermeshed with a 2.0 mm pitch ring roll at 6.3 mm depth of engagement. The raised ridge RKA roll has teeth that are oriented so the long direction runs in the MD, and the ridges and grooves extend circumferentially around the ring roll. The teeth are arranged in a staggered pattern as shown in FIG. 5A. The teeth have a pyramidal shape with 4 sides that taper from the base to a sharp point at the tip, and have a height $h_t$ of 6.9 mm. The teeth have an included angle ($\alpha$ from FIG. 5B) of 57 degrees and a side wall angle on the long side of the tooth of about 5 degrees (β from FIG. 5C). The ridges that span between the teeth on the RKA roll are not rounded and form a flat surface. The teeth are finished at the ridge in the non-truncated format as shown in FIG. 6C. The teeth have an MD tooth spacing $S_{MD}$ tip to tip of 8.0 mm, a cross cut depth ($d_{cc}$ in FIG. 6A) of 3.7 mm and resultant ridge height ($h_R$ in FIG. 6A) of 3.2 mm.

The mating ring roll is 2.0 mm pitch with a height of 6.9 mm, a tip radius of 0.12 mm, and a side wall angle of about 4 degrees. Both rolls have a diameter of about 142 mm. The RKA roll and ring roll are aligned in the CD such that the clearances on either side of the teeth are about equal.

The first precursor web is a polymer film at a basis weight of 25 g/m2, with a blend of LLDPE and LDPE, obtained from Clopay Plastics Co. in Ohio. The precursor web is pre-wrapped on the ring roll prior to passing between the intermeshing rolls at a linear web speed of 20 meters/min. The resultant corrugated, apertured film is shown in FIG. 11 (film is stretched/flattened out to show high and low basis weight regions). Images were taken at low magnification using an optical microscope, such as can be purchased from Allasso Industries, using red LED back lighting.

Figure 19A:
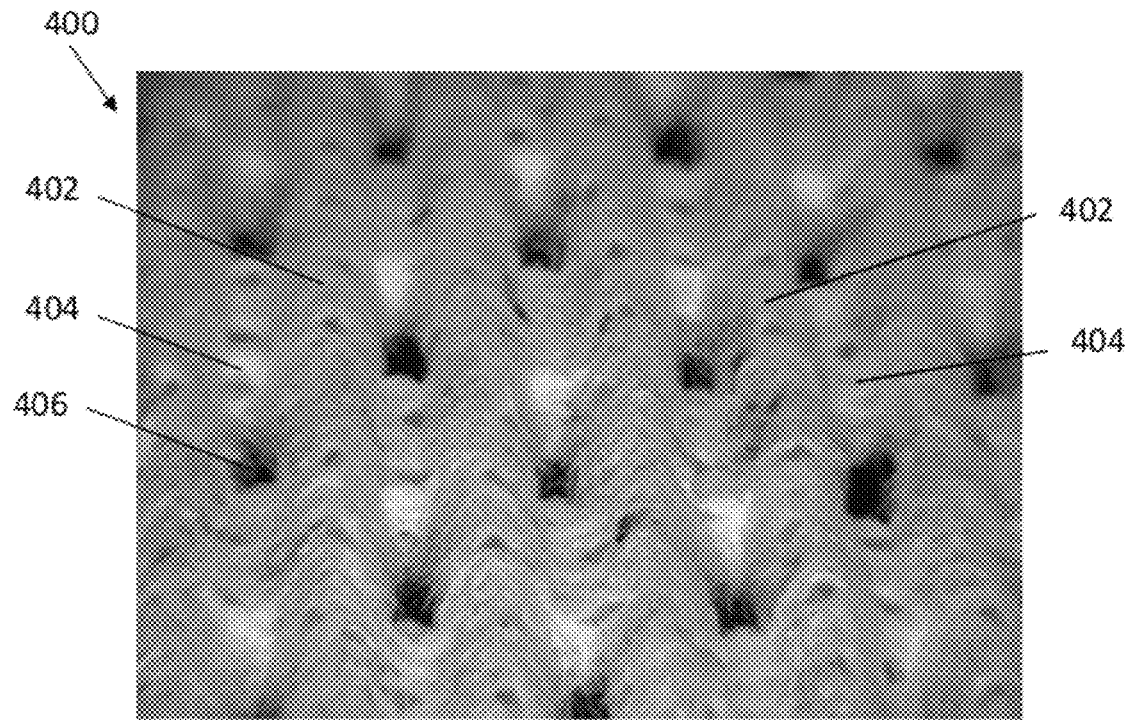
FIG. 19A is a top perspective view of an apertured nonwoven web as described in Example 2.
Figure 19B:
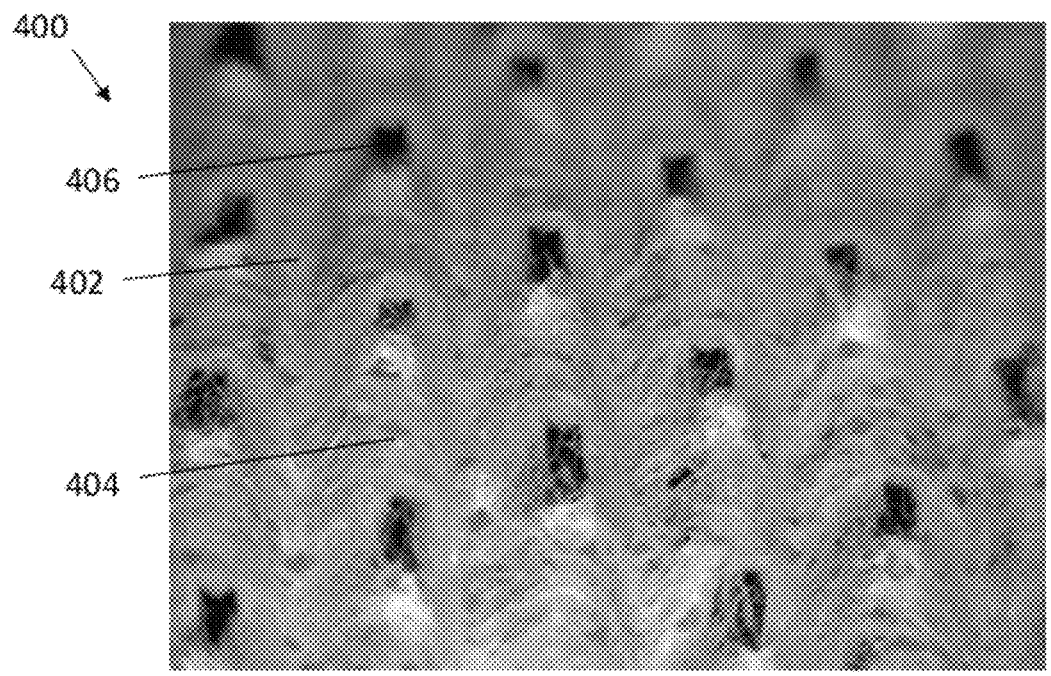
FIG. 19B is a bottom perspective view of the web of FIG. 19A.

The second precursor web is a thermally bonded polypropylene nonwoven at a basis weight of 60 g/m2, obtained from Fiberweb in France. The precursor web is pre-wrapped on the ring roll prior to passing between the intermeshing rolls at a linear web speed of 20 meters/min. The resultant corrugated, apertured nonwoven is shown in FIG. 12 (top view; web is stretched/flattened out to show high and low basis weight regions), FIG. 13 (cross-section view), FIG. 19A (raised-ridge RKA side), and FIG. 19B (ring roll side). Images were taken at low magnification using an optical microscope, such as can be purchased from Allasso Industries. The web 400 in FIGS. 19A and 19B comprises alternating ridges 402 and grooves 404; apertures 406 are present in the grooves 404.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" Furthermore, the numerical ranges recited herein include each discrete numerical value as well as any other narrower range which lies within the range. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for deforming a web using an apparatus, the process comprising feeding a precursor web into a nip that is formed between two intermeshing rolls comprising:
    a) a generally cylindrical first roll, said first roll having a surface, a circumference, and an axis, said first roll comprising:
        1) a plurality of first ridges and first grooves extending around the circumference of the roll on the surface of the roll, wherein said first ridges have a top surface and said first grooves have a bottom surface; and
        2) a plurality of spaced-apart teeth extending outwardly from the top surface of said first ridges, said teeth having tips and a tooth height from 1 mm to 12 mm, wherein the top surface of said first ridges are disposed between the tips of said teeth and the bottom surface of said first grooves, and wherein the top surface is from at least about 25 percent to 95 percent of the tooth height; and
    b) a generally cylindrical second roll, said second roll comprising a plurality of continuous, circumferential second ridges and second grooves, wherein said second ridges have a top surface and said second grooves have a bottom surface;
    wherein when said web is fed into said nip, the top of at least some of the ridges on the first roll extend inward toward the axis of said second roll to a depth beyond the top of at least some of the second ridges on said second roll, and said web is: (i) apertured by said teeth in a plurality of spaced-apart first locations to form a plurality of spaced-apart apertures; and (ii) stretched in the cross-machine direction by said intermeshing rolls.

2. The process of claim 1, wherein at least the first roll or the second roll also forms a nip with one or more additional rolls to thereby further stretch or deform the web.

3. The process of claim 1, wherein the precursor web and intermeshing rolls are not heated.

4. The process of claim 1, wherein the precursor web is heated by wrapping it around a roll heated to 50-200 degC.

5. The process of claim 1, wherein the web comprises a nonwoven; a laminate; a film selected from the group consisting of LLDPE, LDPE, HDPE; or combinations thereof.

* * * * *